(12) United States Patent
Yeomans et al.

(10) Patent No.: US 8,258,096 B2
(45) Date of Patent: *Sep. 4, 2012

(54) THERAPY PROCEDURE FOR DRUG DELIVERY FOR TRIGEMINAL PAIN

(75) Inventors: David C. Yeomans, Sunnyvale, CA (US); William H. Frey, II, White Bear Lake, MN (US); Daniel I. Jacobs, Mountain View, CA (US); Martin S. Angst, Palo Alto, CA (US)

(73) Assignees: The Board of Trustees of the Leland Stanford Junior University, Palo Alto, CA (US); Trigemina, Inc., Mountain View, CA (US); HealthPartners Research Foundation, Bloomington, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/165,646

(22) Filed: Jun. 21, 2011

(65) Prior Publication Data

US 2011/0250212 A1 Oct. 13, 2011

Related U.S. Application Data

(63) Continuation of application No. 12/409,413, filed on Mar. 23, 2009, now abandoned, which is a continuation of application No. 11/990,878, filed as application No. PCT/US2006/033672 on Aug. 28, 2006, now abandoned.

(60) Provisional application No. 60/794,004, filed on Apr. 21, 2006, provisional application No. 60/711,950, filed on Aug. 26, 2005.

(51) Int. Cl.
*A61K 38/11* (2006.01)
*A61K 51/00* (2006.01)
*A61P 5/10* (2006.01)
*C07K 7/16* (2006.01)

(52) U.S. Cl. ...................................... 514/11.6; 530/315

(58) Field of Classification Search ........................ None
See application file for complete search history.

(56) References Cited

U.S. PATENT DOCUMENTS

| | | | |
|---|---|---|---|
| 2,938,891 A | 5/1960 | Velluz et al. |
| 3,076,797 A | 2/1963 | Velluz et al. |
| 4,213,968 A | 7/1980 | Kastin et al. |
| 4,464,378 A | 8/1984 | Hussain |
| 4,486,441 A | 12/1984 | Fozard et al. |
| 4,885,287 A | 12/1989 | Hussain et al. |
| 5,624,898 A | 4/1997 | Frey, II |
| 5,656,721 A | 8/1997 | Albert et al. |
| 5,859,048 A | 1/1999 | Oohashi et al. |
| 6,054,462 A | 4/2000 | Francois et al. |
| 6,090,368 A | 7/2000 | Zia et al. |
| 6,139,861 A | 10/2000 | Friedman |
| 6,143,278 A | 11/2000 | Elkhoury |
| 6,166,039 A | 12/2000 | Yaksh |
| 6,180,603 B1 | 1/2001 | Frey, II |
| 6,262,021 B1 | 7/2001 | Uvnas-Moberg et al. |
| 6,313,093 B1 | 11/2001 | Frey, II |
| 6,342,478 B1 | 1/2002 | Frey, II |
| 6,407,061 B1 | 6/2002 | Frey, II |
| 6,413,499 B1 | 7/2002 | Clay |
| 6,677,346 B1 | 1/2004 | Achari et al. |
| 6,815,424 B2 | 11/2004 | Vickery et al. |
| 6,825,203 B2 | 11/2004 | Pasternak et al. |
| 6,881,423 B2 | 4/2005 | Dohi et al. |
| 6,991,785 B2 | 1/2006 | Frey, II |
| 7,273,618 B2 | 9/2007 | Frey, II et al. |
| 7,452,868 B2 | 11/2008 | Kuzma et al. |
| 2001/0043915 A1 | 11/2001 | Frey, II |
| 2001/0055607 A1 | 12/2001 | Levin |
| 2002/0028786 A1 | 3/2002 | Frey, II et al. |
| 2002/0072498 A1 | 6/2002 | Frey, II |
| 2002/0082215 A1 | 6/2002 | Frey, II |
| 2002/0141971 A1 | 10/2002 | Frey, II |
| 2002/0169102 A1 | 11/2002 | Frey, II |
| 2003/0072793 A1 | 4/2003 | Frey, II et al. |
| 2003/0077300 A1 | 4/2003 | Wermeling |
| 2003/0104085 A1 | 6/2003 | Yeomans |
| 2003/0119892 A1 | 6/2003 | Caldwell et al. |
| 2003/0165434 A1 | 9/2003 | Reinhard et al. |
| 2003/0185872 A1 | 10/2003 | Kochinke |
| 2003/0215398 A1 | 11/2003 | Frey, II |
| 2003/0223981 A1 | 12/2003 | Mochly-Rosen et al. |
| 2003/0229025 A1 | 12/2003 | Xiao et al. |
| 2004/0105889 A1 | 6/2004 | Ryde et al. |
| 2004/0120896 A1 | 6/2004 | Dugger, III |
| 2004/0204366 A1 | 10/2004 | Pasternak et al. |
| 2004/0258757 A1 | 12/2004 | Bosch et al. |
| 2005/0142072 A1 | 6/2005 | Birch et al. |
| 2005/0153885 A1 | 7/2005 | Yun et al. |
| 2005/0272642 A1 | 12/2005 | Frey, II et al. |
| 2006/0009413 A1 | 1/2006 | Frey, II et al. |
| 2006/0009414 A1 | 1/2006 | Frey, II et al. |
| 2006/0014716 A1 | 1/2006 | Frey, II et al. |
| 2006/0030542 A1 | 2/2006 | Frey, II et al. |
| 2006/0039995 A1 | 2/2006 | Frey, II et al. |
| 2006/0135437 A1 | 6/2006 | Stoehr et al. |

(Continued)

FOREIGN PATENT DOCUMENTS

DE 43 12 913 A1 10/1994

(Continued)

OTHER PUBLICATIONS

Robbins Headache Clinic. Combination therapy for headaches. http://www.headachedrugs.com/archives2/combination.html.*

(Continued)

*Primary Examiner* — Maury Audet
(74) *Attorney, Agent, or Firm* — Morrison & Foerster LLP

(57) ABSTRACT

The present invention relates to methods for the treatment or prevention of trigeminal nerve-associated pain, in particular chronic, acute and procedural-related pain. The methods comprise administration of analgesic agents to the trigeminal nerve system which results in analgesia to the facial or head region.

19 Claims, 8 Drawing Sheets

U.S. PATENT DOCUMENTS

| | | | |
|---|---|---|---|
| 2006/0159626 | A1 | 7/2006 | Frey, II |
| 2006/0188496 | A1 | 8/2006 | Bentz et al. |
| 2006/0216317 | A1 | 9/2006 | Reinhard et al. |
| 2006/0252685 | A1* | 11/2006 | Gould ............................. 514/12 |
| 2007/0004743 | A1 | 1/2007 | Xiao et al. |
| 2007/0054843 | A1 | 3/2007 | Yeomans et al. |
| 2007/0093420 | A1 | 4/2007 | Yeomans et al. |
| 2009/0181880 | A1 | 7/2009 | Yeomans et al. |
| 2009/0291900 | A1 | 11/2009 | Yeomans et al. |
| 2009/0317377 | A1 | 12/2009 | Yeomans et al. |
| 2010/0080797 | A1 | 4/2010 | Yeomans et al. |

FOREIGN PATENT DOCUMENTS

| | | | |
|---|---|---|---|
| EP | 1 468 690 | A1 | 10/2004 |
| EP | 1 928 484 | B1 | 11/2008 |
| JP | 2001-2589 | A | 1/2001 |
| JP | 2001-89359 | A | 4/2001 |
| JP | 2001-527537 | A | 12/2001 |
| JP | 2005-500258 | A | 1/2005 |
| JP | 2009-506071 | A | 2/2009 |
| JP | 2009-506076 | A | 2/2009 |
| WO | WO-86/06959 | A1 | 12/1986 |
| WO | WO-91/07947 | A1 | 6/1991 |
| WO | WO-93/15737 | A1 | 8/1993 |
| WO | WO-93/17037 | A1 | 9/1993 |
| WO | WO-94/21286 | A1 | 9/1994 |
| WO | WO-98/42275 | A1 | 10/1998 |
| WO | WO-98/43660 | A1 | 10/1998 |
| WO | WO-00/33813 | A1 | 6/2000 |
| WO | WO-00/33814 | A2 | 6/2000 |
| WO | WO-00/33814 | A3 | 6/2000 |
| WO | WO-01/41732 | A1 | 6/2001 |
| WO | WO-02/076388 | A2 | 10/2002 |
| WO | WO-02/076388 | A3 | 10/2002 |
| WO | WO-02/082074 | A1 | 10/2002 |
| WO | WO-02/086105 | A1 | 10/2002 |
| WO | WO-03/072056 | A1 | 9/2003 |
| WO | WO-03/093816 | A2 | 11/2003 |
| WO | WO-03/093816 | A3 | 11/2003 |
| WO | WO-2004/019875 | A2 | 3/2004 |
| WO | WO-2004/019875 | A3 | 3/2004 |
| WO | WO-2004/043428 | A2 | 5/2004 |
| WO | WO-2004/043428 | A3 | 5/2004 |
| WO | WO-2004/062563 | A2 | 7/2004 |
| WO | WO-2004/062563 | A3 | 7/2004 |
| WO | WO-2004/093897 | A1 | 11/2004 |
| WO | WO-2005/115370 | A2 | 12/2005 |
| WO | WO-2005/115370 | A3 | 12/2005 |
| WO | WO-2006/020727 | A2 | 2/2006 |
| WO | WO-2006/091332 | A2 | 8/2006 |
| WO | WO-2006/091332 | A3 | 8/2006 |
| WO | WO-2007/025249 | A2 | 3/2007 |
| WO | WO-2007/025249 | A3 | 3/2007 |
| WO | WO-2007/025286 | A2 | 3/2007 |
| WO | WO-2007/025286 | A3 | 3/2007 |

OTHER PUBLICATIONS

Zubrzycka et al. (Inhibition of trigemino-hypoglossal reflex in rats by oxytocin is mediated by mu and kappa opioid receptors. Brain Res. Feb. 21, 2005;1035(1):67-72.*

Aboufatima, R. et al. (Apr. 8, 2004). "No Tolerance to the Antinociceptive Action of Calcitonin in Rats and Mice," *Neurosci. Lett.* 359(1-2):5-8.

Abouleish, E. (Nov.-Dec. 1976). "Postpartum Hypertension and Convulsion After Oxytocic Drugs," *Anesth. Analg.* 55(6):813-815.

Ågren, G. et al. (Sep. 29, 1997). "Olfactory Cues from an Oxytocin-Injected Male Rat Can Induce Anti-Nociception in its Cagemates," *Neuroreport* 8(14):3073-3076.

Agu, R.U. et al. (2004). "Metabolism and Absorption Enhancement of Methionine Enkephalin in Human Nasal Epithelium," *Peptides* 25:563-569.

Amico, J.A. et al. (Nov. 1983). "A Time-Dependent Peak of Oxytocin Exists in Cerebrospinal Fluid but Not in Plasma of Humans," *J. Clin. Endocrinol. Metab.* 57(5):947-951.

Arletti, R. et al. (Mar. 1993). "Influence of Oxytocin on Nociception and Morphine Antinociception," *Neuropeptides* 24(3):125-129.

Beck, E. et al. (Feb. 15, 2005). "Management of Cluster Headache," *American Family Physician* 71(4):717-724.

Bessette, L. et al. (1998). "A Placebo Controlled Crossover Trial of Subcutaneous Salmon Calcitonin in the Treatment of Patients with Fibromyalgia," *Scand. J. Rheumatol.* 27(2):112-116.

Born, J. et al. (Jun. 2002). "Sniffing Neuropeptides: A Transnasal Approach to the Human Brain," *Nat. Neurosci.* 5(6):514-516.

Braga, P.C. et al. (Mar. 5, 1993). "Antinociceptive Activity of Salmon Calcitonin: Electrophysiological Correlates in a Rat Chronic Pain Model," *Neurosci. Lett.* 151(1):85-88.

Calvin, W.H. et al. (Apr. 1977). "A Neurophysiological Theory for the Pain Mechanism of Tic Douloureux," *Pain* 3(2):147-154.

Candeletti, S. et al. (Feb. 1992). "Intracerebroventricular Salmon Calcitonin Reduces Autotomy Behavior in Rats After Dorsal Rhizotomy," *Pain* 48(2):275-278.

Capsoni, S. et al. (2009). "Delivery of NGF to the Brain: Intranasal Versus Ocular Administration in Anti-NGF Transgenic Mice," *Journal of Alzheimer's Disease* 16:371-388.

Carlton, S.M. et al. (Jun. 1, 2001). "Tonic Control of Peripheral Cutaneous Nociceptors by Somatostatin Receptors," *J. Neurosci.* 21(11):4042-4049.

Carlton, S.M. et al. (2004). "Somatostatin Modulates the Transient Receptor Potential Vanilloid 1 (TRPV1) Ion Channel," *Pain* 110(3):616-627.

Brown, D.C. et al. (1998). "Oxytocin Content of the Cerebrospinal Fluid of Dogs and its Relationship to Pain Induced by Spinal Cord Compression," *Vet. Surg.* 27(6):607-611.

Carr, D.B. et al. (2004). "Safety and Efficacy of Intranasal Ketamine for the Treatment of Breakthrough Pain in Patients with Chronic Pain: a Randomized, Double-Blind, Placebo-Controlled, Crossover Study," *Pain* 108(1-2):17-27.

Carstens, J.H. Jr. et al. (1991). "Future Horizons for Calcitonin: A U.S. Perspective," *Calcif. Tissue Int.* 49(Suppl. 2):S2-S6.

Chevillard, C. et al. (1984). "Angiotensin-Converting Enzyme in Discrete Forebrain Areas of Spontaneously Hypertensive Rats," *Brain Res.* 309:389-392.

Condés-Lara, M. et al. (Jun. 20, 2003). "Actions of Oxytocin and Interactions with Glutamate on Spontaneous and Evoked Dorsal Spinal Cord Neuronal Activities," *Brain Res.* 976(1):75-81.

Condés-Lara, M. et al. (May 31, 2005). "Oxytocin Actions on Afferent Evoked Spinal Cord Neuronal Activities in Neuropathic but not in Normal Rats," *Brain Res.* 1045(1-2):124-133.

Condés-Lara, M. et al. (Apr. 7, 2006). "Paraventricular Hypothalamic Influences on Spinal Nociceptive Processing," *Brain Res.* 1081(1):126-137.

Copp, D.H. (Jun. 1994). "Calcitonin: Discovery, Development, and Clinical Application," *Clin. Invest. Med.* 17(3):268-277.

De Fraissinette, A. et al. (Oct. 1995). "In vitro Tolerability of Human Nasal Mucosa: Histopathological and Scanning Electron-Microscopic Evaluation of Nasal Forms Containing Sandostatin®," *Cell Biol. Toxicol.* 11(5):295-301.

Eggers, T.R. et al. (Feb. 1979). "Water Intoxication and Syntocinon Infusion," *Aust. N.Z. J. Obstet. Gynecol.* 19(1):59-60.

Epperson, C.N. et al. (1996). "Intranasal Oxytocin in Obsessive-Compulsive Disorder," *Biol. Psychiatry* 40(6):547-549.

Epperson, C.N. et al. (1996). "Intranasal Oxytocin in Trichotillomania," *Biol. Psychiatry* 40(6):559-560.

Ezzat, S. et al. (Nov. 1, 1992). "Octreotide Treatment of Acromegaly. A Randomized, Multicenter Study," *Annals of Internal Medicine* 117(9):711-718.

Fabbri, A. et al. (Sep. 23, 1985). "Calcitonin Receptors in the Rat Mesencephalon Mediate its Analgesic Actions: Autoradiographic and Behavioral Analyses," *Brain Res.* 343(2):205-215.

Fanciullacci, M. et al. (1997). "Responsiveness of the Trigeminovascular System to Nitroglycerine in Cluster Headache Patients," *Brain* 120:283-288.

Fassler, J.E. et al. (1990). "Octreotide Inhibits Increases in Short-Circuit Current Induced in Rat Colon by VIP, Substance P, Serotonin and Aminophylline," *Regulatory Peptides* 29(2-3):189-197.

Final Office Action mailed on Sep. 8, 2009, for U.S. Appl. No. 11/381,383, filed May 3, 2006, 25 pages.

Final Office Action mailed on Jun. 24, 2010, for U.S. Appl. No. 12/210,866, filed Sep. 15, 2008, 9 pages.

Final Office Action mailed on Jul. 6, 2010, for U.S. Appl. No. 12/409,419, filed Mar. 23, 2009, 9 pages.

Fischer, M.J.M. et al. (Jun. 22, 2005). "The Nonpeptide Calcitonin Gene-Related Peptide Receptor Antagonist BIBN4096BS Lowers the Activity of Neurons with Meningeal Input in the Rat Spinal Trigeminal Nucleus," *The Journal of Neuroscience* 25(25):5877-5883.

Flood, P. et al. (Dec. 2004). "Intranasal Nicotine for Postoperative Pain Treatment," *Anesthesiology* 101(6):1417-1421.

Frey, W.H. II (Jul./Aug. 2002). "Bypassing the Blood-Brain Barrier to Deliver Therapeutic Agents to the Brain and Spinal Cord," *Drug Delivery Technology* 2(5):46-49.

Gabopoulou, Z. et al. (Dec. 2002). "Epidural Calcitonin: Does it Provide Better Postoperative Analgesia? an Analysis of the Haemodynamic, Endocrine, and Nociceptive Responses of Salmon Calcitonin and Opioids in Epidural Anesthesia for Hip Arthroplasty Surgery," *Pain Pract.* 2(4):326-331.

Gaginella, T.S. et al. (Sep. 1990). "Treatment of Endocrine and Nonendocrine Secretory Diarrheal States with Sandostatin®," *Metabolism: Clinical and Experimental* 39(9 Suppl 2):172-175.

Gao, L. et al.(2004). "Involvement of Opioid Receptors in the Oxytocin-Induced Antinociception in the Central Nervous System of Rats," *Regulatory Peptides* 120:53-58.

Gazelius, B. et al. (1981). "Evidence that Substance P is a Mediator of Antidromic Vasodilatation Using Somatostatin as a Release Inhibitor," *Acta Physiologica Scandinavica* 113(2):155-159.

Ge, Y. et al. (Feb. 15, 2002). "Blockade Effect of mu and kappa Opioid Antagonists on the Anti-Nociception Induced by Intra-Periaqueductal Grey Injection of Oxytocin in Rats," *Brain Res.* 927(2):204-207.

Ghai, B. et al. (Oct.-Dec. 2004). "Complex Regional Pain Syndrome: A Review," *J. Postgraduate Medicine* 50(4):300-307.

Gimpl, G. et al. (Apr. 2001). "The Oxytocin Receptor System: Structure, Function and Regulation," *Physiol. Rev.* 81 (2):629-683.

Goadsby, P.J. (2005). "New Targets in the Acute Treatment of Headache," *Current Opinion in Neurology* 18(3):283-288.

Goadsby, P.J. (Apr. 2005). "Migraine Pathophysiology," *Headache* 45(Suppl.1):S14-S24.

Gobelet, C. et al. (Sep. 1986). "Calcitonin and Reflex Sympathetic Dystrophy Syndrome," *Clin. Rheumatol.* 5(3):382-388.

Goodlin, R.C. (Dec. 15, 1985). "Is Oxytocin the Culprit?" *Am. J. Obstet Gynecol.* 153(8):928-929.

Guidobono, F. et al. (Mar.-Apr. 1986). "Eel Calcitonin Binding Site Distribution and Antinociceptive Activity in Rats," *Peptides* 7(2):315-322.

Gupta, D.R. et al. (May 1, 1972). "Oxytocin, 'Salting Out,' and Water Intoxication," *JAMA* 220(5):681-683.

Gwak, H.S. et al. (2003). "Analgesic Effects of Intra-Nasal Enkephalins," *J. Pharm. Pharmacol.* 55:1207-1212.

Hackler, L. et al. (1997). "Isolation of Relatively Large Amounts of Endomorphin-1 and Endomorphin-2 From Human Brain Cortex," *Peptides* 18(10):1635-1639. (from spec.).

Haldemann, A.R. et al. (Mar. 1995). "Somatostatin Receptor Scintigraphy in Central Nervous System Tumors: Role of Blood-Brain Barrier Permeability," *J. Nucl. Med.* 36(3):403-410.

Hamamci, N. et al. (Oct.-Nov. 1996). "Calcitonin Treatment in Reflex Sympathetic Dystrophy: A Preliminary Study," *Br. J. Clin. Pract.* 50(7):373-375.

Harris, R.E. (Jun. 1970). "Water Intoxication Secondary to Oxytocin," *VA Med. Mon.* 97(6):357-359.

Heinrichs, M. et al. (Oct. 30, 2004). "Selective Amnesic Effects of Oxytocin on Human Memory," *Physiol Behav.* 83(1):31-38.

Helmchen, C. et al. (1995). "Inhibition of Spinal Nociceptive Neurons by Microinjections of Somatostatin into the Nucleus Raphe Magnus and the Midbrain Periaqueductal Gray of the Anesthetized Cat," *Neuro. Lett.* 187(2):137-141.

Helyes, Z. et al. (1996). "Anti-Inflammatory and Antinociceptive Effect of Different Somatostatin-Analogs," *Neurobiology* 4(1-2):115-117.

Helyes, Z. et al. (2000). "Anti-Nociceptive Effect Induced by Somatostatin Released from Sensory Nerve Terminals and by Synthetic Somatostatin Analogues in the Rat," *Neuro. Lett.* 278(3):185-188.

Helyes, Z. et al. (2001). "Anti-Inflammatory Effect of Synthetic Somatostatin Analogues in the Rat," *British Journal of Pharmacology* 134(7):1571-1579.

Helyes, Z. et al. (May 2004). "Antiinflammatory and Analgesic Effects of Somatostatin Released from Capsaicin-Sensitive Sensory Nerve Terminals in a Freund's Adjuvant-Induced Chronic Arthritis Model in the Rat," *Arthritis and Rheumatism* 50(5):1677-1685.

Hoover, R.T. (1971). "Intranasal Oxytocin in Eighteen Hundred Patients. A Study on its Safety as Used in a Community Hospital," *Am. J. Obstet. Gynecol.* 110(6):788-794.

Hruby, V.J. et al. (Jul.-Sep. 1989). "Recent Developments in the Design of Receptor Specific Opioid Peptides," *Medicinal Research Reviews* 9(3):343-401.

Hunter, D.D. et al. (1998). "Identification and Neuropeptide Content of Trigeminal Neurons Innervating the Rat Nasal Epithelium," *Neuroscience* 83(2):591-599.

Illum, L. (Jan. 2004). "Is Nose-To-Brain Transport of Drugs in Man a Reality?" *J. Pharm. Pharmacol.* 56(1):3-17.

International Search Report mailed on Feb. 16, 2007, for PCT Patent Application No. PCT/US2006/033500, filed on Aug. 28, 2006, four pages.

International Search Report mailed on Mar. 2, 2007, for PCT Patent Application No. PCT/US2006/033672, filed on Aug. 28, 2006, six pages.

Invitti, C. et al. (1996). "Effect of Chronic Treatment with Octreotide Nasal Powder on Serum Levels of Growth Hormone, Insulin-Like Growth Factor I, Insulin-Like Growth Factor Binding Proteins 1 and 3 in Acromegalic Patients," *J. Endocrino. Invest.* 19(8):548-555.

Jaeger, H. et al. (Jan. 1992). "Calcitonin in Phantom Limb Pain: a Double-Blind Study," *Pain* 48(1):21-27.

Jallad, R.S. et al. (2005). "Treatment of Acromegaly with Octreotide-LAR: Extensive Experience in a Brazilian Institution," *Clinical Endocrinology* 63(2):168-175.

Jo, Y-H. et al. (Apr. 1, 1998). "Oxytocin Modulates Glutamatergic Synaptic Transmission Between Cultured Neonatal Spinal Cord Dorsal Horn Neurons," *J. Neurosci.* 18(7):2377-2386.

Josey, W.E. et al. (Jul. 15, 1969). "Oxytocin-Induced Water Intoxication," *Am. J. Obstet. Gynecol.* 104(6):926.

Kang, Y.S. et al. (2000). "Brain Uptake and the Analgesic Effect of Oxytocin—its Usefulness as an Analgesic Agent," *Arch. Pharm. Res.* 23(4):391-395.

Kapicioglu, S. et al. (1997). "Treatment of Migraine Attacks with a Long-Acting Somatostatin Analogue (Octreotide, SMS 201-995)," *Cephalalgia* 17(1):27-30 (eight pages).

Kaplan, E. (Jan. 7, 1978). "A Generalized Epileptiform Convulsion After Intra-Amniotic Prostaglandin with Intravenous Oxytocin Infusion: A Case Report," *S. Afr. Med. J.* 53(1):27-29.

Katai, M. et al. (2005). "Octreotide as a Rapid and Effective Painkiller for Metastatic Carcinoid Tumor," *Endocrine Journal* 52(2):277-280.

Kirsch, P. et al. (Dec. 7, 2005). "Oxytocin Modulates Neural Circuitry for Social Cognition and Fear in Humans," *J. Neurosci.* 25(49):11489-11493.

Kitazawa, T. et al. (1998). "Efflux of Taurocholic Acid Across the Blood-Brain Barrier: Interaction with Cyclic Peptides," *The Journal of Pharmacology and Experimental Therapeutics* 286(2):890-895.

Kosfeld, M. et al. (Jun. 2, 2005). "Oxytocin Increases Trust in Humans," *Nature* 435:673-676.

Lamberts, S.W.J. (1988). "The Role of Somatostatin in the Regulation of Anterior Pituitary Hormone Secretion and the Use of Its Analogs in the Treatment of Human Pituitary Tumors," *Endocrine Reviews* 9(4):417-436.

Lamberts, S.W.J. et al. (Jan. 25, 1996). "Octreotide," *The New England Journal of Medicine* 334(4):246-254.

Landgraf, R. (1985). "Plasma Oxytocin Concentrations in Man After Different Routes of Administration of Synthetic Oxytocin," *Exp. Clin. Endocrinol.* 85(2):245-248.

Lee, H.M. et al. (Nov. 28, 2003). "Diclofenac Inhibition of Sodium Currents in Rat Dorsal Root Ganglion Neurons," *Brain Res.* 992(1):120-127.

Lerner, E.N. (Jun. 2004). "Enhanced Delivery of Octreotide to the Brain via Transnasal Iontophoretic Administration," *Journal of Drug Targeting* 12(5):273-280.

Levy, M.J. et al. (Jul.-Aug. 2003). "Acromegaly: A Unique Human Headache Model," *Headache* 43(7):794-797.

Levy, M.J. et al. (2003). "Somatostatin Infusion Withdrawal: A Study of Patients with Migraine, Cluster Headache and Healthy Volunteers," *Pain* 102(3):235-241.

Levy, M.J. et al. (2005). "Octreotide is not Effective in the Acute Treatment of Migraine," *Cephalalgia* 25(1):48-55.

Levy, M.J. et al. (Aug. 2005; e-pub. May 11, 2005). "The Clinical Characteristics of Headache in Patients with Pituitary Tumours," *Brain* 128(Pt. 8):1921-1930.

List, M.A. et al. (2000). "Evaluation of Quality of Life in Patients Definitely Treated for Squamous Carcinoma of the Head and Neck," *Curr. Opin. Oncol.* 12:215-220.

Loup, F. et al. (Oct. 23, 1989). "Localization of Oxytocin Binding Sites in the Human Brainstem and Upper Spinal Cord: An Autoradiographic Study," *Brain Res.* 500(1-2):223-230.

Loup, F. et al. (Aug. 2, 1991). "Localization of High-Affinity Binding Sites for Oxytocin and Vasopressin in the Human Brain. An Autoradiographic Study," *Brain Res.* 555(2):220-232.

Lundeberg, T. et al. (Mar. 28, 1994). "Anti-Nociceptive Effects of Oxytocin in Rats and Mice," *Neurosci. Lett.* 170(1):153-157.

Lussier, D. et al. (2004). "Adjuvant Analgesics in Cancer Pain Management," *The Oncologist* 9(5):571-591.

Lustig, R.H. et al. (2006; e-pub. Sep. 13, 2005). "A Multicenter, Randomized, Double-Blind, Placebo-Controlled, Dose-Finding Trial of a Long-Acting Formulation of Octreotide in Promoting Weight Loss in Obese Adults with Insulin Hypersecretion," *International Journal of Obesity* 30(2):331-341.

Lyritis, G.P. et al. (1997). "Pain Relief from Nasal Salmon Calcitonin in Osteoporotic Vertebral Crush Fractures. A Double Blind, Placebo-Controlled Clinical Study," *Acta Orthop. Scand.* 68(Suppl.275):112-114.

Madrazo, I. et al. (1987). "Intraventricular Somatostatin-14, Arginine Vasopressin, and Oxytocin: Analgesic Effect in a Patient with Intractable Cancer Pain," *Appl. Neurophysiol.* 50(1-6):427-431.

Maeda, Y. et al. (1994). "Inhibitory Effects of Salmon Calcitonin on the Tail-Biting and Scratching Behavior Induced by Substance P and Three Excitatory Amino Acids," *J. Neural Transm.* (Gen. Sect.) 96(2):125-133.

Matharu, M.S. et al. (Oct. 2004; e-pub. Sep. 30, 2004). "Subcutaneous Octreotide in Cluster Headache: Randomized Placebo-Controlled Double-Blind Crossover Study," *Ann. Neurol.* 56(4):488-494.

Matharu, M.S. et al. (Nov. 2004). "Subcutaneous Octreotide in Cluster Headache: Randomized Placebo-Controlled Double-Blind Crossover Study," Erratum, *Ann. Neurol.* 56(5):751.

McKenna, P. et al. (Nov.-Dec. 1979). "Hyponatremic Fits in Oxytocin-Augmented Labors," *Int. J. Gynaecol. Obstet.* 17(3):250-252.

Mens, W.B.J. et al. (Feb. 28, 1983). "Penetration of Neurohypophyseal Hormones from Plasma into Cerebrospinal Fluid (CSF): Half-Times of Disappearance of These Neuropeptides from CSF," *Brain Res.* 262(1):143-149.

Meunier, A. (Apr. 2005). Attenuation of Pain-Related Behaviour in a Rat Model of Trigeminal Neuropathic Pain by Viral-Driven Enkephalin Overproduction in Trigeminal Ganglion Neurons, *Molecular Therapy* 11(4):608-616.

Millan, M.J. et al. (Sep. 19, 1984). "Vasopressin and Oxytocin in the Rat Spinal Cord: Analysis of Their Role in the Control of Nociception," *Brain Res.* 309(2):384-388.

Miralles, F.S. et al. (Jul. 1987). "Postoperative Analgesia Induced by Subarachnoid Lidocaine Plus Calcitonin," *Anesth. Analg.* 66(7):615-618.

Musolino, N.R. et al. (1990). "Headache in Acromegaly: Dramatic Improvement with the Somatostatin Analogue SMS 201-995," *The Clinical Journal of Pain* 6(3):243-245.

Newman, C.B. et al. (Sep. 1998). "Octreotide as Primary Therapy for Acromegaly," *The Journal of Clinical Endocrinology and Metabolism* 83(9):3034-3040.

Non-Final Office Action mailed on Mar. 21, 2008, for U.S. Appl. No. 11/511,997, filed Aug. 28, 2006, 6 pages.

Non-Final Office Action mailed on Dec. 3, 2009, for U.S. Appl. No. 12/409,419, filed Mar. 23, 2009, 6 pages.

Non-Final Office Action mailed on Feb. 4, 2010, for U.S. Appl. No. 12/210,866, filed Sep. 15, 2008, 6 pages.

Non-Final Office Action mailed Dec. 23, 2010, for U.S. Appl. No. 12/409,413, filed Mar. 23, 2009, 8 pages.

Non-Final Office Action mailed on Dec. 27, 2010, for U.S. Appl. No. 11/990,878, filed Aug. 19, 2009, 10 pages.

Non-Final Office Action mailed on Nov. 30, 2011, for U.S. Appl. No. 13/269,527, filed Oct. 7, 2011, 9 pages.

Non-Final Office Action mailed on Dec. 23, 2011, for U.S. Appl. No. 12/210,866, filed Sep. 15, 2008, 14 pages.

Non-Final Office Action mailed on Dec. 23, 2011, for U.S. Appl. No. 12/409,419, filed Mar. 23, 2009, 14 pages.

Non-Final Office Action mailed on Feb. 13, 2012, for U.S. Appl. No. 13/269,527, filed Oct. 7, 2011, 10 pages.

Ofluoglu, D. et al. (Jan. 2007; e-pub. Mar. 31, 2006). "The Effect of Calcitonin on β-Endorphin Levels in Postmenopausal Osteoporotic Patients with Back Pain," *Clin. Rheumatol.* 26(1):44-49.

Olesen, J. (2004). "The International Classification of Headache Disorders," *Cephalalgia* 24(Suppl. 1):1-151.

Paice, J.A. et al. (Jan. 1996). "Intrathecal Octreotide for Relief of Intractable Nonmalignant Pain: 5-Year Experience with Two Cases," *Neurosurgery* 38(1):203-207, located at <http://gateway.ut.ovid.com/gw1/ovidweb.cgi>, last visited Mar. 30, 2007, ten pages.

Parker, K.J. et al. (Oct. 2005). "Intranasal Oxytocin Administration Attenuates the ACTH Stress Response in Monkeys," *Psychoneuroendocrinology* 30(9):924-929.

Pascual, J. et al. (1991). "Analgesic Effect of Octreotide in Headache Associated with Acromegaly is not Mediated by Opioid Mechanisms. Case Report," *Pain* 47(3):341-344.

Pawlak, M. et al. (2004). "Octreotide, a Somatostatin Analogue, Attenuates Movement Evoked Discharges of Fine Afferent Units from Inflamed Knee Joints of Rats," *Neuro. Lett.* 361(1-3):180-183.

Pedlow, P.R.B. (Dec. 1970). "Syntocinon Induced Convulsion," *J. Obstet. Gynecol. Br. Commonw.* 77(12):1113-1114.

Penn, R.D. et al. (Apr. 1992). "Octreotide: A Potent New Non-Opiate Analgesic for Intrathecal Infusion," *Pain* 49(1):13-19.

Petersson, M. et al. (Jul. 12, 1996). "Oxytocin Increases Nociceptive Thresholds in a Long-Term Perspective in Female and Male Rats," *Neurosci. Lett.* 212(2):87-90.

Petersson, M. et al. (Aug. 16, 2005). "Oxytocin Decreases Corticosterone and Nociception and Increases Motor Activity in OVX Rats," *Maturitas* 51(4):426-433.

Phillips, W.J. et al. (2006). "Relief of Acute Migraine Headache with Intravenous Oxytocin: Report of Two Cases," *J. Pain Palliat. Care Pharmacother.* 20(3):25-28.

Potter, R.R. (May 1964). "Water Retention Due to Oxytocin," *Obstet. Gynecol.* 23(5):699-702.

Randić, M. et al. (1978). "Depressant Actions of Methionine-Enkephalin and Somatostatin in Cat Dorsal Horn Neurones Activated by Noxious Stimuli," *Brain Res.* 152(1):196-202.

Reiter, M.K. et al. (Jan. 1, 1994). "Localization of Oxytocin Binding Sites in the Thoracic and Upper Lumbar Spinal Cord of the Adult and Postnatal Rat: A Histoautoradiographic Study," *Eur. J. Neurosci.* 6(1):98-104.

Robinson, D.A. et al. (Apr. 15, 2002). "Oxytocin Mediates Stress-Induced Analgesia in Adult Mice," J. Physiol. 540(Pt. 2):593-606.

Ross, T.M. et al. (2004). "Intranasal Administration of Interferon Beta Bypasses the Blood-Brain Barrier to Target the Central Nervous System and Cervical Lymph Nodes: A Non-Invasive Treatment Strategy for Multiple Sclerosis," *Journal of Neuroimmunology* 151:66-77.

Sahin, F. et al. (Mar. 2006; e-pub. Jun. 25, 2005). "Efficacy of Salmon Calcitonin in Complex Regional Pain Syndrome (Type 1) in Addition to Physical Therapy," *Clin. Rheumatol.* 25(2):143-148.

Sakurada, S. et al. (2002). "Recent Advances in the Search for the μ-Opioidergic System: Differential Antinociceptive Effects Induced by Intrathecally-Administered Endomorphin-1 and Endomorphin-2 in Mice," *Jpn. J. Pharmacol.* 89:221-223.

Sances, G. et al. (Apr. 2003). "Course of Migraine During Pregnancy and Postpartum: A Prospective Study," *Cephalalgia* 23(3):197-205.

Sandler, L.M. et al. (1987). "Effective Long-Term Treatment of Acromegaly with a Long-Acting Somatostatin Analogue (SMS 201-995)," *Clinical Endocrinology* 26(1):85-95.

Sayani, A.P. et al. (1996). "Systemic Delivery of Peptides and Proteins Across Absorptive Mucosae," *Critical Reviews in Therapeutic Drug Carrier Systems* 13(1&2):85-184.

Schindler, M. et al. (1997). "Immunohistochemical Localization of the Somatostatin $SST_{2(A)}$ Receptor in the Rat Brain and Spinal Cord," *Neuroscience* 76(1):225-240.

Schindler, M. et al. (1998). "Identification of Somatostatin $sst_{2(a)}$ Receptor Expressing Neurones in Central Regions Involved in Nociception," *Brain Res.* 798(1-2):25-35.

Schmidt, K. et al. (May 1993). "Analgesic Effect of the Somatostatin Analogue Octreotide in Two Acromegalic Patients: A Double-Blind Study with Long-Term Follow-up," *Pain* 53(2):223-227.

Schmidt, M. et al. (Jul. 1998). "Somatostatin Receptor Imaging in Intracranial Tumours," *European Journal of Nuclear Medicine* 25(7):675-686.

Schwartz, G. et al. (1996). "Effects of Salmon Calcitonin on Patients with Atypical (Idiopathic) Facial Pain: A Randomized Controlled Trial," *J. Orofac. Pain* 10(4):306-315.

Schwetz, I. et al. (2004). "Anti-Hyperalgesic Effect of Octreotide in Patients with Irritable Bowel Syndrome," *Alimentary Pharmacology & Therapeutics* 19(1):123-131.

Seifer, D.B. et al. (Mar. 1985). "Water Intoxication and Hyponatremic Encephalopathy from the Use of an Oxytocin Nasal Spray," *J. Repro. Med.* 30(3):225-228.

Selmer, I. et al. (2000). "Advances in Understanding Neuronal Somatostatin Receptors," *Regulatory Peptides* 90(1-3):1-18.

Selmer, I-S. et al. (2000). "First Localisation of Somatostatin $sst_4$ Receptor Protein in Selected Human Brain Areas: An Immunohistochemical Study," *Mol. Brain Res.* 82(1-2):114-125.

Sibilia, V. et al. (2000). "Amylin Compared with Calcitonin: Competitive Binding Studies in Rat Brain and Antinociceptive Activity," *Brain Res.* 854(1-2):79-84.

Sicolo, N. et al. (1990). "Analgesic Effect of Sandostatin (SMS 201-995) on Acromegaly Headache," *Minerva Endocrinol.* 15(1):37-42. (Article in Italian, Abstract in English.).

Sicuteri, F. et al. (1984). "Pain Relief by Somatostatin in Attacks of Cluster Headache," *Pain* 18(4):359-365.

Strassman, A.M. et al. (Mar. 2006). "Response Properties of Dural Nociceptors in Relation to Headache," *J. Neurophysiol.* 95(3):1298-1306.

Striebel, H.W. et al. (1996). "Patient-Controlled Intranasal Analgesia: A Method for Noninvasive Postoperative Pain Management," *Anesth. Analg.* 83:548-551.

Szolcsányi, J. et al. (1998). "Release of Somatostatin and Its Role in the Mediation of the Anti-Inflammatory Effect Induced by Antidromic Stimulation of Sensory Fibres of Rat Sciatic Nerve," *British Journal of Pharmacology* 123(5):936-942.

Szolcsányi, J. et al. (1998). "Systemic Anti-Inflammatory Effect Induced by Counter-Irritation Through a Local Release of Somatostatin from Nociceptors," *British Journal of Pharmacology* 125(4):916-922.

Tafazal, S.I. et al. (Feb. 2007). "Randomised Placebo-Controlled Trial on the Effectiveness of Nasal Salmon Calcitonin in the Treatment of Lumbar Spinal Stenosis," *Eur. Spine J.* 16(2):207-212.

Thán, M. et al. (Jul. 7, 2000). "Systemic Anti-Inflammatory Effect of Somatostatin Released from Capsaicin-Sensitive Vagal and Sciatic Sensory Fibres of the Rat and Guinea-Pig," *European Journal of Pharmacology* 399(2-3):251-258.

Thorne, R.G. (2004). "Delivery of Insulin-Like Growth Factor-I to the Rat Brain and Spinal Cord Along Olfactory and Trigeminal Pathways Following Intranasal Administration," *Neuroscience* 127:481-496.

Truini, A. et al. (Sep. 2005). "New Insight into Trigeminal Neuralgia," *J. Headache Pain* 6(4):237-239.

Tsavaris, N. et al. (2006). "Analgesic Activity of High-Dose Intravenous Calcitonin in Cancer Patients with Bone Metastases," *Oncol. Rep.* 16(4):871-875.

Tseng, L.F. (2002). "Recent Advances in the Search for the µ-Opioidergic System: The Antinociceptive Properties of Endomorphin-1 and Endomorphin-2 in the Mouse," *Jpn. J. Pharmacol.* 89:216-220.

Tzabazis, A. et al. (2005). "Differential Activation of Trigeminal C or Aδ Nociceptors by Infrared Diode Laser in Rats: Behavioral Evidence," *Brain Res.* 1037:148-156. (received from D. Pardi and D. Pardi 3/18 e-mail list.)

Uhl-Bronner, S. et al. (2005). "Sexually Dimorphic Expression of Oxytocin Binding Sites in Forebrain and Spinal Cord of the Rat," *Neuroscience* 135(1):147-154.

Uryvaev, Y.V. et al. (Nov. 1996). "Extremely Low Doses of Oxytocin Reduce Pain Sensitivity in Men," *Bulletin of Experimental Biology and Medicine* 122(5):1071-1073. (Translated from *Byulleten' Eksperimental'noi Biologii i Meditsiny*, 122(11):487-489, Nov. 1996.).

Van Rossum, D. et al. (Sep. 1997). "Neuroanatomical Localization, Pharmacological Characterization and Functions of CGRP, Related Peptides and Their Receptors," *Neurosci. Biohehay. Rev.* 21 (5):649-678.

Visser, E.J. et al. (Oct. 2006). "Salmon Calcitonin in the Treatment of Post Herpetic Neuralgia," *Anaesth. Intensive Care* 34(5):668-671.

Wall, G.C. et al. (Apr. 1999). "Calcitonin in Phantom Limb Pain," *Ann. Pharmacother.* 33(4):499-501.

Wang, Y-C. J. et al. (Nov.-Dec. 1980). "Review of Excipients and pH's for Parenteral Products Used in the United States," *J. Parent Drug. Assn.* 34(6):452-462.

Wang, Y-C. J. et al. (1988). "Parenteral Formulations of Proteins and Peptides: Stability and Stabilizers," *J. Parent Sci. and Tech.* 42(2S):S4-S26.

Wang, J-W. et al. (2003). "Antinociceptive Role of Oxytocin in the Nucleus Raphe Magnus of Rats, an Involvement of µ-opioid Receptor," *Regul. Pept.* 115:153-159.

Weeke, J. et al. (1992). "A Randomized Comparison of Intranasal and Injectable Octreotide Administration in Patients With Acromegaly," *The Journal of Clinical Endocrinology and Metabolism* 75(1):163-169.

Wermeling, D.P. et al. (Nov. 4, 2005). "Analgesic Effects of Intranasal Butorphanol Tartrate Administered via a Unit-Dose Device in the Dental Impaction Pain Model: A Randomized, Double-Blind, Placebo-Controlled, Parallel-Group Study," *Clinical Therapeutics* 27(4):430-440.

Whitfield, M.F. et al. (1980). "Accidental Administration of Syntometrine in Adult Dosage to the Newborn," *Arch. Dis. Child.* 55:68-70.

Wiesenfeld-Hallin, Z. et al. (Sep. 17, 1984). "Subarachnoid Injection of Salmon Calcitonin Does Not Induce Analgesia in Rats," *Eur. J. Pharmacol.* 104(3-4):375-377.

Williams, G. et al. (Oct. 30, 1986). "Improvement in Headache Associated with Prolactinoma During Treatment with a Somatostatin Analogue: an "N of 1" Study," *The New England Journal of Medicine* 315(18):1166-1167.

Williams, G. et al. (Jul. 25, 1987). "Analgesic Effect of Somatostatin Analogue (Octreotide) In Headache Associated with Pituitary Tumours," *British Medical Journal (Clinical Research Ed.)* 295(6592):247-248.

Windle, R.J. et al. (Mar. 24, 2004). "Oxytocin Attenuates Stress-Induced *c-fos* mRNA Expression in Specific Forebrain Regions Associated with Modulation of Hypothalamo-Pituitary-Adrenal Activity," *J. Neurosci.* 24(12):2974-2982.

Witt, D.M. (Jan. 15, 1997). "Regulatory Mechanisms of Oxytocin-Mediated Sociosexual Behavior," *Ann. N.Y. Acad. Sci.* 807:287-301.

Woodhouse, D.R. (Jan. 12, 1980.) "Water Intoxication Associated with High Dose Syntocinon Infusion," *Med. J. Aust.* 1(1):34.

Yang, J. (Apr. 15, 1994). "Intrathecal Administration of Oxytocin Induces Analgesia in Low Back Pain Involving the Endogenous Opiate Peptide System," *Spine* 19(8):867-871.

Young, E.A. (2001)."Effects of Estrogen Antagonists and Agonists on the ACTH Response to Restraint Stress in Female Rats," *Neuropsychopharmacology* 25(6):881-891.

Yu, S-Q. et al. (Sep. 5, 2003). "Involvement of Oxytocin in Spinal Antinociception in Rats with Inflammation," *Brain Res.* 983:13-22.

Zadina, J.E. et al. (Apr. 3, 1997). "A Potent and Selective Endogenous Agonist for the µ-Opiate Receptor," *Nature* 386:499-502.

* cited by examiner

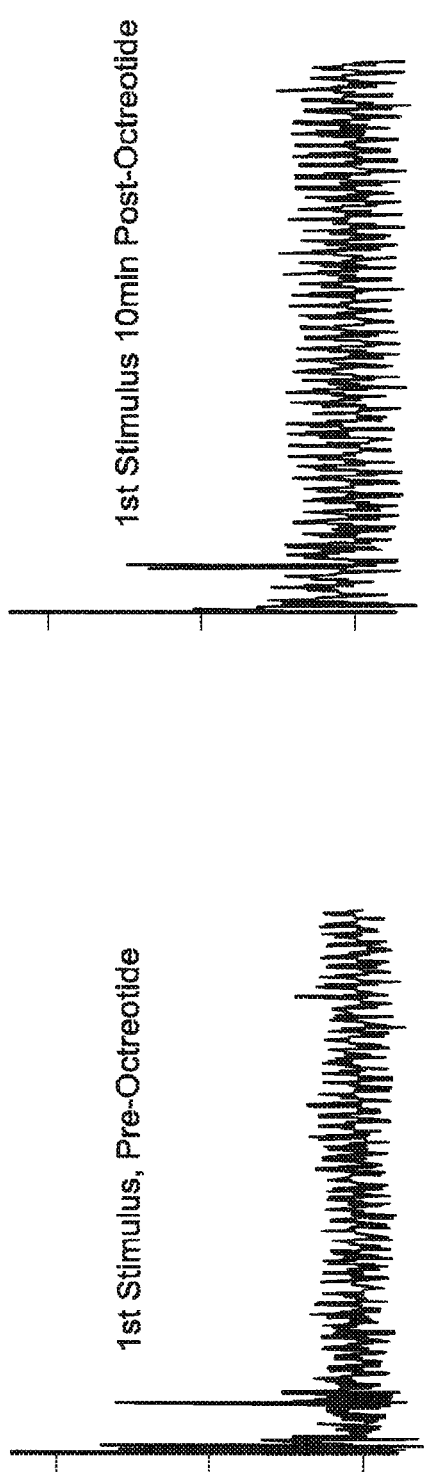
FIG. 5C
FIG. 5E
FIG. 5D
FIG. 5F

SEQUENCE LISTING

```
<160> NUMBER OF SEQ ID NOS: 28

<210> SEQ ID NO 1
<211> LENGTH: 5
<212> TYPE: PRT
<213> ORGANISM: Artificial Sequence
<220> FEATURE:
<223> OTHER INFORMATION: Synthetic peptide

<400> SEQUENCE: 1

Tyr Gly Gly Phe Leu
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic peptide

<400> SEQUENCE: 2

Tyr Gly Gly Phe Met
1               5
```

<210> SEQ ID NO 3
<211> LENGTH: 36
<212> TYPE: PRT
<213> ORGANISM: Artificial Sequence
<220> FEATURE:
<223> OTHER INFORMATION: Synthetic peptide

<400> SEQUENCE: 3

Tyr Gly Gly Phe Met Lys Lys Met Asp Glu Leu Tyr Pro Leu Glu Val
 1               5                  10                  15

Glu Glu Glu Ala Asn Gly Gly Phe Val Leu Gly Lys Arg Thr Arg Tyr
            20                  25                  30

Gly Gly Phe Met
        35

<210> SEQ ID NO 4
<211> LENGTH: 31
<212> TYPE: PRT
<213> ORGANISM: Homo sapiens

<400> SEQUENCE: 4

Tyr Gly Gly Phe Met Thr Ser Glu Lys Ser Gln Thr Pro Leu Val Thr
 1               5                  10                  15

Leu Phe Lys Asn Ala Ile Ile Lys Asn Ala Tyr Lys Lys Gly Glu
            20                  25                  30

<210> SEQ ID NO 5
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: AMIDATION
<222> LOCATION: 15

<400> SEQUENCE: 5

Tyr Gly Gly Phe Met Thr Ser Glu Ser Gln Thr Pro Leu Val Thr
 1               5                  10                  15

<210> SEQ ID NO 6
<211> LENGTH: 17
<212> TYPE: PRT
<213> ORGANISM: Artificial Sequence
<220> FEATURE:
<223> OTHER INFORMATION: Synthetic peptide

<400> SEQUENCE: 6

Tyr Gly Gly Phe Leu Arg Arg Ile Arg Pro Lys Leu Lys Trp Asp Asn
 1               5                  10                  15

Gln

<210> SEQ ID NO 7
<211> LENGTH: 13
<212> TYPE: PRT
<213> ORGANISM: Artificial Sequence
<220> FEATURE:
<223> OTHER INFORMATION: Synthetic peptide

<400> SEQUENCE: 7

Tyr Gly Gly Phe Leu Arg Arg Gln Phe Lys Val Val Thr
 1               5                  10

<210> SEQ ID NO 8
<211> LENGTH: 10

```
<212> TYPE: PRT
<213> ORGANISM: Artificial Sequence
<220> FEATURE:
<223> OTHER INFORMATION: Synthetic peptide

<400> SEQUENCE: 8

Tyr Gly Gly Phe Leu Arg Lys Tyr Pro Lys
 1               5                  10

<210> SEQ ID NO 9
<211> LENGTH: 9
<212> TYPE: PRT
<213> ORGANISM: Artificial Sequence
<220> FEATURE:
<223> OTHER INFORMATION: Synthetic peptide

<400> SEQUENCE: 9

Tyr Gly Gly Phe Leu Arg Lys Tyr Pro
 1               5

<210> SEQ ID NO 10
<211> LENGTH: 8
<212> TYPE: PRT
<213> ORGANISM: Artificial Sequence
<220> FEATURE:
<223> OTHER INFORMATION: Synthetic peptide

<400> SEQUENCE: 10

Tyr Gly Gly Phe Leu Arg Arg Ile
 1               5

<210> SEQ ID NO 11
<211> LENGTH: 13
<212> TYPE: PRT
<213> ORGANISM: Artificial Sequence
<220> FEATURE:
<223> OTHER INFORMATION: Synthetic peptide

<400> SEQUENCE: 11

Tyr Gly Gly Phe Leu Arg Arg Ile Arg Pro Lys Leu Lys
 1               5                  10

<210> SEQ ID NO 12
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: AMIDATION
<222> LOCATION: 4

<400> SEQUENCE: 12

Tyr Pro Trp Phe
 1

<210> SEQ ID NO 13
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: AMIDATION
<222> LOCATION: 4

<400> SEQUENCE: 13

Tyr Pro Phe Phe
 1
```

```
<210> SEQ ID NO 14
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: 2
<223> OTHER INFORMATION: Xaa = (D)Ala
<220> FEATURE:
<221> NAME/KEY: AMIDATION
<222> LOCATION: 7

<400> SEQUENCE: 14

Tyr Xaa Phe Gly Tyr Pro Ser
 1               5

<210> SEQ ID NO 15
<211> LENGTH: 7
<212> TYPE: PRT
<213> ORGANISM: Bovine

<400> SEQUENCE: 15

Tyr Pro Phe Pro Gly Pro Ile
 1               5

<210> SEQ ID NO 16
<211> LENGTH: 7
<212> TYPE: PRT
<213> ORGANISM: Homo sapiens

<400> SEQUENCE: 16

Tyr Pro Phe Val Glu Pro Ile
 1               5

<210> SEQ ID NO 17
<211> LENGTH: 3
<212> TYPE: PRT
<213> ORGANISM: Artificial Sequence
<220> FEATURE:
<223> OTHER INFORMATION: Synthetic peptide

<400> SEQUENCE: 17

Tyr Pro Phe
 1

<210> SEQ ID NO 18
<211> LENGTH: 4
<212> TYPE: PRT
<213> ORGANISM: Artificial Sequence
<220> FEATURE:
<223> OTHER INFORMATION: Synthetic peptide

<400> SEQUENCE: 18

Tyr Pro Phe Pro
 1

<210> SEQ ID NO 19
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: AMIDATION
<222> LOCATION: 4
```

```
<400> SEQUENCE: 19

Tyr Pro Phe Pro
 1

<210> SEQ ID NO 20
<211> LENGTH: 5
<212> TYPE: PRT
<213> ORGANISM: Artificial Sequence
<220> FEATURE:
<223> OTHER INFORMATION: Synthetic peptide

<400> SEQUENCE: 20

Tyr Pro Phe Pro Gly
 1               5

<210> SEQ ID NO 21
<211> LENGTH: 8
<212> TYPE: PRT
<213> ORGANISM: Artificial Sequence
<220> FEATURE:
<223> OTHER INFORMATION: Synthetic peptide

<400> SEQUENCE: 21

Tyr Pro Phe Pro Gly Pro Ile Pro
 1               5

<210> SEQ ID NO 22
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: 2
<223> OTHER INFORMATION: Xaa = (D)Ala
<220> FEATURE:
<221> NAME/KEY: AMIDATION
<222> LOCATION: 7

<400> SEQUENCE: 22

Tyr Xaa Phe Asp Val Val Gly
 1               5

<210> SEQ ID NO 23
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: 2
<223> OTHER INFORMATION: Xaa = (D)Ala
<220> FEATURE:
<221> NAME/KEY: AMIDATION
<222> LOCATION: 7

<400> SEQUENCE: 23

Tyr Xaa Phe Glu Val Val Gly
 1               5

<210> SEQ ID NO 24
<211> LENGTH: 7
<212> TYPE: PRT
<213> ORGANISM: Artificial Sequence
<220> FEATURE:
<223> OTHER INFORMATION: Synthetic peptide
```

```
<220> FEATURE:
<221> NAME/KEY: VARIANT
<222> LOCATION: 2
<223> OTHER INFORMATION: Xaa = (D)Met
<220> FEATURE:
<221> NAME/KEY: AMIDATION
<222> LOCATION: 7

<400> SEQUENCE: 24

Tyr Xaa Phe His Leu Met Asp
 1               5

<210> SEQ ID NO 25
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: 2
<223> OTHER INFORMATION: Xaa = (D)Ala

<400> SEQUENCE: 25

Tyr Xaa Phe Gly Tyr Pro Ser
 1               5

<210> SEQ ID NO 26
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: AMIDATION
<222> LOCATION: 4

<400> SEQUENCE: 26

Tyr Pro Phe Pro
 1

<210> SEQ ID NO 27
<211> LENGTH: 9
<212> TYPE: PRT
<213> ORGANISM: Artificial Sequence
<220> FEATURE:
<223> OTHER INFORMATION: Synthetic peptide

<400> SEQUENCE: 27

Cys Tyr Ile Gln Asn Cys Pro Leu Gly
 1               5

<210> SEQ ID NO 28
<211> LENGTH: 4
<212> TYPE: PRT
<213> ORGANISM: Artificial Sequence
<220> FEATURE:
<223> OTHER INFORMATION: Synthetic peptide

<400> SEQUENCE: 28

Tyr Gly Gly Phe
 1
```

THERAPY PROCEDURE FOR DRUG DELIVERY FOR TRIGEMINAL PAIN

CROSS-REFERENCE TO RELATED APPLICATIONS

This application is a continuation of U.S. patent application Ser. No. 12/409,413, filed Mar. 23, 2009, which is a continuation of U.S. patent application Ser. No. 11/990,878, with an International filing date of Aug. 28, 2006, which is a national Phase filing under 35 U.S.C. §371 of International Application No. PCT/US2006/033672, filed Aug. 28, 2006, which is related to and claims the benefit of U.S. Provisional Patent Application Ser. No. 60/711,950, filed Aug. 26, 2005, and U.S. Provisional Patent Application Ser. No. 60/794,004, filed Apr. 21, 2006, the entire contents of which are hereby incorporated by reference herein in their entirety.

TECHNICAL FIELD

The present invention relates generally to methods and compositions for the treatment of pain. More specifically, the present invention relates to methods for the treatment prevention of trigeminal nerve-associated procedural, acute and chronic pain by administration and targeted delivery of analgesic agents to the trigeminal nerve system resulting in localized pain relief with minimal untoward central nervous system effects or systemic side effects.

BACKGROUND OF THE INVENTION

Pain is experienced when the free nerve endings which constitute the pain receptors in the skin as well as in certain internal tissues are subjected to mechanical, thermal, chemical or other noxious stimuli. The pain receptors (nociceptors) can transmit signals along afferent neurons into the central nervous system and then to the brain. The causes of pain can include inflammation, injury, disease, muscle spasm and the onset of a neuropathic event or syndrome. Ineffectively treated pain can be devastating to the person experiencing it by limiting function, reducing mobility, complicating sleep, and dramatically interfering with the quality of life.

The trigeminal sensory nerves (afferents) innervate and transmit to the brain most of the sensory signals from the face and anterior head. Pain involving the trigeminal nerve and ganglion arises in many different medical situations and presents unique problems to pain therapists and doctors. Chronic pain due to syndromes such as trigeminal neuralgia, atypical facial pain, anesthesia dolorosa, post-herpetic neuralgia, cancer of the head and neck, migraine headaches, and temporomandibular joint pain are examples of very different pain syndromes that all involve the trigeminal system and which present clinical challenges that are peculiar to this nerve distribution. In addition to chronic pain states, there are clinical situations where facial and head pain is associated with acute trauma such as an abscessed tooth, a headache or a direct injury to the face and/or head such as a laceration or a burn. Further, medical procedures such as common dental work and facial plastic and/or cosmetic surgery may elicit considerable pain, as well as discomfort and anxiety.

Among syndromes associated with facial pain is trigeminal neuralgia, also called "tic duloreaux" which is among the most debilitating facial pain syndromes. Trigeminal neuralgia usually begins after the age of 40, is slightly more common in women and has an incidence of approximately 4-5 per 100,000 persons (Khorami and Totals (2001) *eMedicine Journal*, Vol. 2). The primary symptom of trigeminal neuralgia is the sudden onset of severe, sharp facial pain, usually without warning. The quick bursts of pain are described as "lightening bolt-like", "machine gun-like" or "electric shock-like". The pain is generally on one side of the face and is spasmodic, coming in short bursts lasting a few seconds which may repeat many times over the course of a day. Trigeminal neuralgia can involve one or more branches of the trigeminal nerve and the causes are varied. Pharmacologic treatments include anti-seizure medications such as carbamazepine (Tegretol, Carbatrol), phenyloin (Dilantin), clonazepam (Klonopin), gabapentin (Neurontin), and lamtrignine (Lamictal), tricyclic antidepressants such as amitriptyline (Elavil) and muscle relaxants such as baclofen. The treatments generally have limited efficacy and many patients eventually undergo an invasive procedure. The procedural interventions often involve the direct manipulation of the trigeminal ganglion and include microvascular decompression, alcohol injection aimed at destroying pain fibers, glycerol injection aimed at selectively destroying pain-transmitting fibers, percutaneous radiofrequency rhizotomy, pulse radio frequency and gamma-knife. The pain relief from these procedures can be successful in a percentage of these patients, but the relief can be short-lived and often facial pain returns. Significant procedural pain and long term morbidity may also be associated with such treatments.

Atypical Facial Pain (ATFP) is a syndrome encompassing a wide group of facial pain problems. ATFP can have many different causes but the symptoms are all similar. Facial pain, often described as burning, aching or cramping, occurs on one side of the face, often in the region of the trigeminal nerve and can extend into the upper neck or back of the scalp. Although rarely as severe as trigeminal neuralgia, facial pain is continuous for ATFP patients, with few, if any periods of remission. Some studies propose that ATFP is an early form of trigeminal neuralgia, but there is no agreement at this time. Drug treatments for ATFP are similar to what is prescribed for trigeminal neuralgia including anti-seizure medications and tricyclic antidepressants with limited effectiveness.

Anesthesia dolorosa is one of the most dreaded complications of neurosurgery and is considered to be non-reversible. The two main symptoms of anesthesia dolorosa are facial numbness (much like the numbness from a dental anesthetic injection) and constant pain. The pain is usually burning, pulling or stabbing but can also include a sharp, stinging, shooting or electrical component. Pressure and "heaviness" can also be part of the pain symptoms and often there is eye pain. Cold can increase the feeling of numbness sometimes making the face feel frozen. Anesthesia dolorosa occurs when the trigeminal nerve is damaged by surgery, physical trauma or as a complication of surgery to correct a condition such as trigeminal neuralgia. Topical treatments with capsaicin are used to help manage the pain and discomfort, while topical clonidine has been tested in a few cases but no single treatment has been found that resolves all of the pain of this condition.

Post-herpetic neuralgia is pain that remains after the rash from shingles (herpes zoster) has healed. Shingles is an infection of the nerves caused by the varicella-zoster virus, which is the same virus that causes chickenpox. About one-third of the people who get shingles will get post herpetic neuralgia. The pain of post herpetic neuralgia may be constant, stabbing, aching, or burning and can last for months to years after the shingles outbreak.

It is predicted that approximately 65,000 Americans will be diagnosed with head and neck cancers this year, this represents about 3% of all cancers diagnosed in the United States (American Cancer Society). Close to 60% of head and neck cancer patients report long-term pain with up to 25% claiming moderate or severe pain (List and Stracks (2000) *Curr. Opin. Oncol.,* 12:215-20). The trigeminal nerves and ganglion are likely to mediate most of the head and facial pain in these patients and sometimes are directly affected by the cancerous growth. The recommended treatment for most cancer patients with mild to severe pain is opioid therapy such as hydrocodone, codeine, oxycodone, morphine, fentanyl and hydromorphone. Opioid therapy has a multitude of problems including systemic effects away from the site of pain stimulation. Furthermore, opioids are highly addictive and patients build up tolerance to the drugs quickly resulting in higher and higher doses being administered.

Migraine headaches affect more than 29.5 million people in the United States. The typical migraine headache is throbbing or pulsatile, it builds up over a period of 1-2 hours and lasts from several hours to a whole day. Pain intensity is moderate to severe and can be debilitating and often causes nausea and vomiting. Of particular interest to clinicians who study migraine headaches is the superior trigeminal division (the ophthalmic division). This division innervates the forehead, eyebrow, eyelid, anterior scalp, nose and contents of the orbit thus giving an explanation for the pain localization along with the visual aura that is common with migraine headaches. Common treatments for migraine headaches include beta-blockers such as propranolol (Inderal) and Atenolol, tricyclic antidepressants, triptans, ergotamines, anti-seizure drugs and calcium channel blockers. Many of these drugs have systemic side effects and limited effectiveness.

Acute facial pain can arise in patients undergoing common dental procedures such as tooth extraction, root canal surgery and surgery for dental implants and dental prostheses. Acute dental pain can also arise from dental/gingival disease, other conditions such as an abscessed tooth or a bacterial infection or injury, that arise separately from planned dental procedures. Most dentists use topical anesthetics such as benzocaine, eugenol and forms of xylocaine to numb various areas for minor procedures or before injection of a local anesthetic. For most procedures a dentist will inject a local anesthetic such as lidocaine, xylocaine and marcaine to create a nerve block at or around the site where dental work needs to be done. Local anesthetics numb the area where they are injected and eliminate the acute pain of most procedures. In addition to the pain of administration, another main disadvantage of local anesthetics, especially for routine dental procedures, is that numbness and loss of sensation in the facial region will usually last for several hours after the dental procedure is finished.

Facial plastic surgery is becoming a very common procedure with several million procedures done in the United States each year. The procedures range from necessary repair of damage such as lacerations or broken bones to elective cosmetic surgeries such as face lifts, rhinoplasties, skin rejuvenation, etc. For many of these procedures local anesthetics are used (the patients are not under general anesthetic) and as with dental procedures, the local anesthetics can be painful to administer and include the problem of lingering numbness lasting for hours after the procedure is finished. In addition, depending on the surgery performed, patients experience varying levels of post-operative pain after the anesthetic wears off.

Pain treatment of almost any type usually includes some form of analgesic agent or drug. Analgesic drugs are usually classified into three groups: non-opioid drugs, opioid drugs, and co-analgesic drugs, also known as adjuvants. Non-opioid analgesic drugs include acetaminophen and non-steroidal anti-inflammatory drugs or NSAIDs. Opioid drugs, sometimes referred to as "narcotics", include natural substances such as morphine, and semi-synthetic and synthetic substances. Co-analgesic medications are drugs that have a primary use other than pain relief, but also help produce analgesia for some painful conditions.

Opioid drugs are commonly used to relieve pain. However, their usefulness is limited by the tolerance and dependence that normally develops on chronic treatment. Opioid drugs such as morphine can be addictive and can have central nervous system-mediated side effects such as respiratory and cardiac depressions and drowsiness. Additionally, opioid drugs suffer from frequent side effects such as nausea, vomiting and constipation.

Therapeutic drugs are delivered by a number of routes including, for example, oral administration, intravenous injection, intramuscular injection and subcutaneous injection. For patients suffering procedural, acute or chronic pain associated with the trigeminal nerve, one of the main problems with conventional drug delivery with analgesic agents is the lack of localized pain relief due to systemic distribution of the agent. Often larger dosages need to be administered to achieve an effective concentration of the drug at a desired site. With higher doses of an analgesic agent, there is the additional problem of limited efficacy relative to the increase in undesired side effects due to the systemic distribution of the agent. Treatments consisting of localized but invasive interventions directly to the trigeminal nerve have a significant disadvantage due to the lack of selectivity and/or reversibility of the intervention and the fact that these procedures can, by themselves, cause additional facial nerve problems including anesthesia doloroso, persistent numbness and nerve deafferentation. An additional problem with conventional treatments for trigeminal nerve-associated pain, especially with invasive procedures, is the high level of skill, training and equipment required by the medical team which can make treatment expensive and impractical for widespread use.

Intranasal administration has been used for systemic delivery of several therapeutic agents, for example, insulin, thryrotropin-releasing hormone, and vasopressin. Using an intranasal or other mucosal route for systemic delivery of a therapeutic agent allows for ease of administration and the ability to bypass intestinal degradation and first pass hepatic metabolism of the therapeutic agent. There are times when it is desirable to not have systemic distribution of a therapeutic agent or to have a therapeutic agent targeted to a localized or regional area. For example, intranasal drug delivery has been used to bypass the blood-brain barrier and deliver substances to the central nervous system (CNS) and the brain. It has been demonstrated that large molecules such as polypeptides, peptides, oligonucleotides or DNA plasmids can be delivered directly to the CNS via specific uptake routes within the nose such as the axonal and perineural vascular/lymphatic pathways of the olfactory and trigeminal nerves (Frey II (2002) *Drug Delivery Technology,* 2:46-49; Thorne et al. (2004) *Neuroscience,* 127:481-496). However, while there is evidence that various therapeutic agents can be delivered to the brain by an intranasal route and that the agents may travel along perineural pathways, there is no known method utilizing these pathways to specifically target the trigeminal nerve system for localized or regional analgesia in individuals suffering from trigeminal nerve-associated pain.

Despite a wide range of medical treatments, trigeminal nerve-associated pain, in many different forms and situations, continues to affect millions of people. Thus new methods for treating an individual for trigeminal nerve-associated pain are needed to directly target the trigeminal nerve system with analgesic agents and deliver analgesia to facial or head regions with minimal central nervous system effects or systemic side effects.

BRIEF SUMMARY OF THE INVENTION

Provided herein are methods for treating an individual for trigeminal nerve-associated pain, comprising: administering to the individual an effective amount of an analgesic agent wherein the administration is targeted to the trigeminal nerve system and results predominantly in analgesia to the facial or head region, particularly as compared to analgesic effects in other parts of the body. Some aspects of the invention include methods wherein the trigeminal nerve-associated pain is selected from the group consisting of chronic, acute and procedural-related pain and combinations thereof. In some examples, the chronic pain is selected from the group consisting of trigeminal neuralgia, atypical facial pain, anesthesia dolorosa, post-herpetic neuralgia, cancer of the head and neck, migraine headaches, and temporomandibular joint pain. In some examples, the procedural-related pain is pain arising from dental, medical, surgical or cosmetic procedures. In yet other examples, the acute pain is pain arising from a laceration, a burn, a broken bone, an injury, a headache, an abscessed tooth, dental disease, a bacterial infection or a sinus infection.

Provided herein are methods for treating an individual for trigeminal nerve-associated pain, comprising: administering to the individual an effective amount of an analgesic agent wherein the administration is targeted to the trigeminal nerve system and results predominantly in analgesia to the facial or head region and wherein the analgesic agent is administered via mucosal and/or dermal administration. In some examples the analgesic agent is administered intranasally. In other examples the analgesic agent is administered via buccal or sublingual administration. In other examples the analgesic agent is administered to conjunctiva or other mucosal tissues around the eye. In yet other examples the analgesic agent is administered to the skin or dermal surface. In some examples, the analgesic agent is administered by more than one route.

Provided herein are methods for treating an individual for trigeminal nerve-associated pain, comprising: administering to the individual an effective amount of an analgesic agent wherein the administration is targeted to the trigeminal nerve system and results predominantly in analgesia to the facial or head region. Some aspects of the invention include methods wherein the analgesic agent includes, but is not limited to, a peptide, an amino acid, a polypeptide, an opiate or a small molecule compound which has analgesic properties. In some examples the analgesic agent is an opioid peptide selected from a group comprising enkephalins, endorphins, dynorphins, endomorphins, casomorphins, dermorphin, oxytocin and analogues and derivatives thereof. In some examples the analgesic agent is a peptide which inhibits peptidergic enzymes. In other examples the analgesic agent is a peptidergic receptor agonist. In yet other examples the analgesic agent is a peptidergic receptor antagonist. In further examples the analgesic agent is an antibody directed against proalgesic antigens such as endothelin, nerve growth factor, vasoactive intestinal polypeptide (VIP) or pituitary adenylate cyclase-activating polypeptide (PACAP). In some examples the analgesic agent is an antibody directed against calcitonin gene-related peptide (CGRP), cholecystokinin (CCK), Substance P or galanin. In other examples the analgesic agent is a N-methyl-D-aspartate receptor blocker, a non-steroidal anti-inflammatory drug, a steroid anti-inflammatory drug, an ion channel blocker, an antidepressant or an anti-seizure medication. In some examples the analgesic agent is an opioid.

Some aspects of the invention include methods wherein the analgesic agent is administered as a pharmaceutical composition. Accordingly, provided herein are methods for treating an individual for trigeminal nerve-associated pain, comprising: administering to the individual an effective amount of a pharmaceutical composition comprising an analgesic agent wherein the administration is targeted to the trigeminal nerve system and results predominantly in analgesia to the facial or head region. Some aspects of the invention include methods wherein the pharmaceutical composition is administered in a formulation selected from a group comprising a powder, a liquid, a gel, an ointment, a suspension, a film, a foil, a cream or a bioadhesive. Some aspects of the invention include methods wherein the pharmaceutical composition further comprises a protease inhibitor, an absorption enhancer, a vasoconstrictor or combinations thereof. In some examples, the protease inhibitor is selected from a group comprising antipain, arphamenine A and B, benzamidine HCl, AEBSF, CA-074, calpain inhibitor I and II, calpeptin, pepstatin A, actinonin, amastatin, bestatin, chloroacetyl-HOLeu-Ala-Gly-NH$_2$, DAPT, diprotin A and B, ebelactone A and B, foroxymithine, leupeptin, pepstatin A, phosphoramidon, aprotinin, BBI, soybean trypsin inhibitor, phenylmethylsulfonyl fluoride, E-64, chymostatin, 1,10-phenanthroline, EDTA and EGTA. In other examples the absorption enhancer is selected from a group comprising surfactants, bile salts, bioadhesive agents, phospholipid additives, mixed micelles, liposomes, or carriers, alcohols, enamines, cationic polymers, NO donor compounds, long-chain amphipathic molecules, small hydrophobic penetration enhancers; sodium or a salicylic acid derivatives, glycerol esters of acetoacetic acid, cyclodextrin or beta-cyclodextrin derivatives, medium-chain fatty acids, chelating agents, amino acids or salts thereof, N-acetylamino acids or salts thereof, mucolytic agents, enzymes specifically targeted to a selected membrane component, inhibitors of fatty acid synthesis and inhibitors of cholesterol synthesis.

Provided herein are methods for treating an individual for trigeminal nerve-associated pain, comprising: administering to the individual i) an effective amount of a pharmaceutical composition comprising an analgesic agent wherein the administration is targeted to the trigeminal nerve system and results predominantly in analgesia to the facial or head region and ii) a vasoconstrictor wherein administration of the vasoconstrictor reduces systemic distribution of the analgesic agent. In some examples the vasoconstrictor is selected from the group comprising phenylephrine hydrochloride, tetrahydrozoline hydrochloride, naphazoline nitrate, oxymetazoline hydrochloride, tramazoline hydrochloride, endothelin-1, endothelin-2, epinephrine, norepinephrine and angiotensin. In some examples the vasoconstrictor is administered prior to the administration of the pharmaceutical composition. In other examples the vasoconstrictor is co-administered with the pharmaceutical composition. In some examples administration of the vasoconstrictor results in a decreased effective dosage of the analgesic agent.

Provided herein are methods for treating an individual for trigeminal nerve-associated pain, comprising: administering to the individual an effective amount of a pharmaceutical composition comprising an analgesic agent wherein the peptide is administered by buccal or sublingual administration to the oral cavity and wherein the agent preferentially binds to opioid receptors within the trigeminal nerve system and results predominantly in analgesia to the facial or head region. Some aspects provide methods for treating an individual for trigeminal nerve-associated pain, comprising: administering to the individual an effective amount of a pharmaceutical composition comprising an analgesic agent wherein the peptide is administered by transdermal administration to the skin and wherein the agent preferentially binds to opioid receptors within the trigeminal nerve system and results predominantly in analgesia to the facial or head region.

Provided herein are methods for treating an individual for trigeminal nerve-associated pain, comprising: administering to the individual an effective amount of a pharmaceutical composition comprising an analgesic agent wherein the agent is administered by intranasal administration to the nasal cavity and wherein the agent preferentially binds to opioid receptors within the trigeminal nerve system and results predominantly in analgesia to the facial or head region. In some examples the administration is directed to the inferior two-thirds of the nasal cavity. In other examples the administration is directed to the inferior two-thirds of the nasal cavity and is directed away from the olfactory region.

Provided herein are methods for treating an individual for trigeminal nerve-associated pain, comprising: administering to the individual an effective amount of an analgesic agent wherein the administration is targeted to the trigeminal nerve system and results predominantly in analgesia to the facial or head region, particularly as compared to analgesic effects in other parts of the body. In some examples, administration of an analgesic agent or a composition comprising an analgesic agent results in reduction of a pain rating on the VAS of 30% or more. In other examples, administration of an analgesic agent or a composition comprising an analgesic agent results in reduction of a pain rating on the VAS of 50% or more.

Provided are kits for carrying out any of the methods described herein. Kits are provided for use in treatment of trigeminal nerve-associated pain. Kits of the invention may comprise at least one analgesic agent in suitable packaging. Kits may further comprise a vasoconstrictor, at least one protease inhibitor, and/or at least one absorption enhancer. Kits may further comprise a delivery device, including but not limited to, a device for intranasal administration. Kits may further comprise instructions providing information to the user and/or health care provider for carrying out any of the methods described herein.

BRIEF DESCRIPTION OF THE DRAWINGS

FIG. 3 depicts the effect of intranasal administration of oxytocin on electrical stimulus-induced responses of trigeminal nucleus caudalis wide dynamic range neurons.

FIG. 4 depicts the effect of intranasal administration of octreotide on long-pulse laser-induced responses of trigeminal nucleus caudalis wide dynamic range neurons. FIG. 5 depicts the effect of intranasal administration of octreotide on electrical stimulus-induced windup. FIGS. 5C and 5D show the responses to the $1^{st}$ and $15^{th}$ stimuli before octreotide administration. FIGS. 5E and 5F show the responses to the $1^{st}$ and $15^{th}$ stimuli 10 minutes after octreotide administration.

DETAILED DESCRIPTION OF THE INVENTION

Figure 1A:
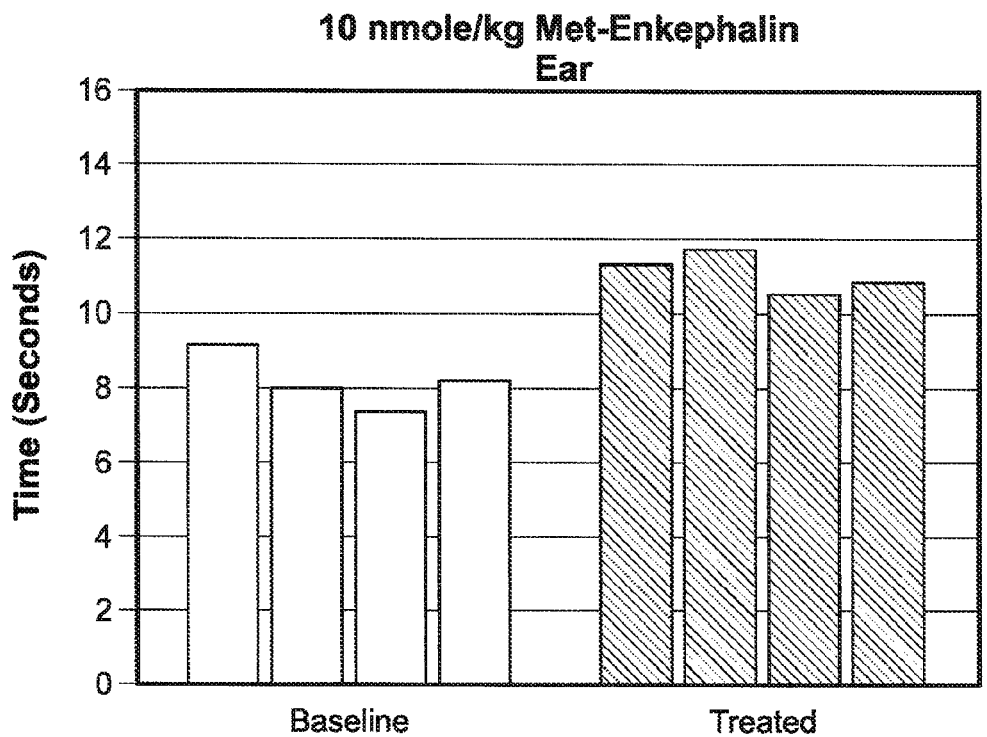
FIG. 1 depicts data demonstrating withdrawal latencies after noxious thermal stimulation to the ears or hindpaws in a rat model after intranasal administration of met-enkephalin. Panel A shows baseline and treated withdrawal latencies after thermal stimulation to the ear. Panel B shows baseline and treated withdrawal latencies after thermal stimulation to the hindpaw. After taking baseline withdrawal latencies, rats were intranasally administered 10 nmoles/kg met-enkephalin and withdrawal latencies were retested. Each bar represents the average, across 4 animals, of latencies in response to stimulation at a particular time after the beginning of the set. Thus, the first white bar in each graph represents responses at the beginning of the baseline testing set; the first black bar represents responses at approximately five minutes after administering met-enkephalin. Each successive bar represents responses at approximately 15 minutes after the previous bar.

Described herein are methods for treating an individual for trigeminal nerve-associated pain. In general, the methods are based on the finding that molecules can travel along perineural pathways to the trigeminal nerve and to the brain. Without wishing to be bound by theory, it is believed that analgesic agents can be targeted to the trigeminal nerve system and that administration of the agents can result in analgesia and pain relief to an individual suffering acute, chronic or procedural facial or head pain. Furthermore, it is believed that targeted drug delivery to the trigeminal nerve system can limit systemic distribution of an analgesic agent which may decrease or eliminate undesirable central nervous system (CNS) effects or systemic side effects. In particular, it is believed that higher concentrations of an analgesic agent at a targeted site will allow for administration of lower dosages of the analgesic agent to the individual.

The methods described herein involve administration of a variety of different analgesic agents to a individual for treatment of trigeminal nerve-associated pain. In general, the methods can administer to the trigeminal nerve an analgesic agent for prevention or treatment of facial or head pain. Administration of analgesic agents targeted for a predominantly regional analgesic effect can result in prevention or alleviation of pain without numbness as compared to local anesthetics. Since the trigeminal nerve transmits most of the sensory signals of the face and head, administration of analgesic agents targeted to the trigeminal nerve can localize the analgesic effect to the face and head region, particularly as compared to analgesic effects in other parts of the body.

Targeted delivery can decrease the amount of agent administered to an individual to achieve an analgesic effect, and can decrease the undesirable CNS effects or systemic side effects of many analgesic agents. More effective or efficient delivery of an analgesic agent to the trigeminal nerve can decrease the total dose of an agent administered to a subject suffering from trigeminal nerve-associated pain. Effective targeted delivery of an analgesic agent to the trigeminal nerve can decrease the systemic distribution of the agent wherein CNS effects or systemic side effects are minimized or eliminated.

In some aspects of the invention are included methods for treating an individual for trigeminal nerve-associated pain comprising administering to the individual an analgesic agent wherein the administration is targeted to the trigeminal nerve system and results predominantly in analgesia to the facial or head region. In some examples, the analgesic agent can be a peptide, in particular an opioid peptide. The opioid peptide can be selected from a group comprising enkephalins, endorphins, α-neoendorphins, dynorphins, endomorphins, casomorphins, deltorphins, dermorphin, oxytocin and analogues and derivatives thereof. In some examples, the peptide can be targeted to opioid receptors on the trigeminal nerves. In other examples, more than one opioid peptide can be administered. In some examples, the analgesic agent can be a non-peptide, such as an amino acid, a polypeptide, an opiate, or a small molecule compound.

Definitions

As used herein, unless otherwise specified, the term "treatment" or "treating pain" refers to administration to an individual an agent of interest wherein the agent alleviates or prevents a pathology for which the subject is being treated. Treatment for trigeminal nerve-associated pain refers to the alleviation or prevention of trigeminal nerve-associated pain.

As used herein, "central nervous system" or "CNS" refers to that part of the nervous system that consists of the brain and spinal cord. The CNS is one of the two major divisions of the nervous system. The other is the peripheral nervous system which is outside of the brain and spinal cord and includes the cranial nerves—of which the trigeminal nerve is a member.

Although analgesia in the strictest sense is an absence of pain, as used herein, "analgesia" refers to reduction in the intensity of the pain perceived by an individual without causing general numbness.

As used herein, "analgesia agent", "analgesic agent" or "analgesic" refers to any biomolecule that alleviates or prevents pain.

As used here, "analgesic peptide" refers to any peptide molecule that alleviates or prevents pain.

As used herein, "opioid peptide" refers to a peptide having a opioid receptor binding moiety and the capacity to bind to an opioid receptor. An opioid peptide can be a naturally occurring endogenous peptide, fragments, analogues or derivatives thereof. An opioid peptide can also be a non-endogenous peptide, fragments, analogues or derivatives thereof.

As used herein, "analogues and derivatives" refers to any peptide analogous to naturally occurring opioid peptides wherein one or more amino acids within the peptide have been substituted, deleted, or inserted. The term also refers to any peptide wherein one or more amino acids have been modified, for example by chemical modification. In general, the term covers all peptides which bind to an opioid receptor and exhibit an opioid activity but which may, if desired, have a different potency or pharmacological profile.

As used herein, "acute pain" refers to sudden, severe pain from a specific cause (injury, infection, inflammation, etc) that lasts a limited period of time (as opposed to chronic pain). As used herein "chronic pain" refers to a persistent state of pain whereby the cause of the pain cannot be easily removed. Chronic pain is often associated with long-term incurable or intractable medical conditions or diseases. As used herein "procedural pain" refers to pain arising from a medical, dental or surgical procedure wherein the procedure is usually planned or associated with acute trauma.

As used herein "systemic side effects" include, but are not limited to, cardiovascular including peripheral vasodilation, reduced peripheral resistance, and inhibition of baroreceptors; dermatologic including pruritus (itching), flushing and red eyes; gastrointestinal including nausea and vomiting, decreased gastric motility in stomach, decreased biliary, pancreatic and intestinal secretions and delays in food digestion in small intestine, diminished peristaltic waves in large intestine contributing to constipation, epigastric distress or biliary colic in biliary tract; respiratory including depressed respiratory rate; and urinary including urinary urgency and difficulty with urination, and peripheral limb heaviness.

As used herein, "central nervous system effects" or "CNS effects" include, but are not limited to, narcosis, euphoria, drowsiness, apathy, psychotic ideation, mental confusion, alteration in mood, reduction in body temperature, feelings of relaxation, dysphoria (an emotional state characterized by anxiety, depression, or unease), nausea and vomiting (caused by direct stimulation of chemoreceptors in the medulla).

As used herein, "mucosal administration" or "administered transmucosally" refers to delivery to the mucosal surfaces of the nose, nasal passageways, nasal cavity; the mucosal surfaces of the oral cavity including the gingiva (gums), the floor of the oral cavity, the cheeks, the lips, the tongue, the teeth; and the mucosal surfaces of or around the eye including the conjunctiva, the lacrimal gland, the nasolacrimal ducts, the mucosa of the upper or lower eyelid and the eye.

As used herein, "intranasal administration" or "administered intranasally" refers to delivery to the nose, nasal passageways or nasal cavity by spray, drops, powder, gel, inhalant or other means.

The nasal cavity contains turbinate bones which protrude in to the nasal cavity and generally separate it into three regions. As used herein, the "inferior two-thirds of the nasal cavity" refers to the portion of the nasal cavity where the middle and inferior turbinate bones protrude and is the region of the nasal cavity that is innervated by the trigeminal nerve system. The superior third of the nasal cavity is defined by the superior turbinate bone wherein the olfactory region is located.

As used herein, "transdermal administration" or "dermal administration" refers to delivery to the skin of the face, neck, scalp or combinations thereof.

As used herein, "pharmaceutically acceptable carrier" or "suitable carrier" refers to a carrier that is conventionally used in the art to facilitate the storage, administration, and/or the healing effect of the agent.

As used herein, "therapeutically effective dose", "therapeutically effective amount" or "an effective amount" refers to an amount of an analgesic agent that is useful for treating pain.

As used herein, "visual analogue scale" (VAS) refers to a commonly used scale in pain assessment. It is a 10 cm horizontal or vertical line with word anchors at each end, such as "no pain" and "pain as bad as it could be". A subject or patient is asked to make a mark on the line to represent pain intensity. This mark is converted to distance in either centimeters or millimeters from the "no pain" anchor to give a pain score that can range from 0-10 cm or 0-100 mm. The VAS may refer to an 11 point numerical pain rating scale wherein 0 equals "no pain" and 10 equals the "worst pain imaginable".

It should be noted that, as used herein, the singular form "a", "an", and "the" includes plural references unless indicated otherwise. Additionally, as used herein, the term "comprising" and its cognates are used in their inclusive sense; that is, equivalent to the term "including" and its corresponding cognates.

Analgesic Agents

Many different classes of molecules are potentially useful for targeted administration to the trigeminal nerve system for the treatment of pain. Certain molecular and biological characteristics make some therapeutic agents particularly unattractive for systemic administration and good candidates for targeted delivery by transdermal and/or transmucosal administration. One characteristic is poor bioavailability of some systemically applied molecules and their lack of ability to reach the target of choice, i.e. the trigeminal nerve system. A second characteristic is the short half-life of some molecules in the systemic circulation and the resulting lack of bioavailability at the desired target, i.e. trigeminal nerve system. Brief half-lives are generally due to rapid degradation of the molecule by enzymes, rapid uptake and turnover in the kidney and/or liver, or excretion via the lung. Targeted delivery by transdermal and/or transmucosal administration can bypass some of these problems. However, targeted delivery is not limited to molecules with these characteristics, rather, these characteristics allow targeted delivery to the trigeminal nerve system, and limit the usefulness of the compounds through other (e.g., systemic) routes of administration.

Opioids are one of the classes of analgesic drugs commonly used for treatment of moderate to severe pain. These compounds include both plant-derived and synthetic alkaloids and also include endogenous peptides found in mammals as well as in lower animals. Examples of opioid analgesics include, but are not limited to, codeine, opium, oxycodone, loperimide, meperidine (Demerol), diphenoxylate, propoxyphene (Darvon), fentanyl, 4-methyl fentanyl, hydrocodone, morphine, diacetylmorphine, dihydrocodeine, hydromorphone (Dilaudid), methadone, levorphanol (Levo-Dromoran), dextromethorphan, oxymorphone (Numorphan), heroin, remifentanil, butorphanol (Torbugesic), phenazocine, pentazocine, piminodine, anileridine, buprenorphine (Suboxone), sufentanil, carfentanil, alfentanil and the atypical opiates, tramadol and tapentadol.

Naturally occurring endogenous opioid peptides can generally be referred to as "endorphins" (endogenous morphines) and include, but are not limited to, beta-endorphin, endomorphins, enkephalins, dynorphins, deltorphins, casomorphins, dermorphin and oxytocin.

Analgesic activity may be mediated by opiate receptors found within the central nervous system and on peripheral neurons throughout the body. Opioid peptides bind to the same opiate receptors as narcotic opioid drugs. Both endogenous peptide opioids and narcotic morphine-like analgesics can alter the central release of neurotransmitters from afferent nerves sensitive to noxious, i.e. painful, stimuli. After binding with a receptor, opioid drugs or peptides may act to initiate or block various biochemical and physiological sequences.

Several major categories of opioid receptors are known: mu (µ), kappa (κ), delta (δ), and epsilon (ε). In general, mu-receptors mediate analgesia, euphoria, respiratory and physical depression, miosis, and reduced GI motility, delta-receptors mediate analgesia, dysphoria, psychotomimetic and respiratory effects and kappa-receptors mediate analgesia, sedation, miosis, respiratory depression and dysphoria. There is a differential distribution of these opiate receptors on nerves throughout the CNS and the peripheral neural system. In particular, mu and delta opioid receptors are found on the nociceptors in the trigeminal nerve but not on the olfactory nerve fibers within the nasal cavity. The differential distribution of opioid receptors can allow for targeted administration of opioid peptides to receptors within the trigeminal nerve while delivery to the olfactory nerve and the brain is minimized.

The peptides for use in the herein described methods can be natural or synthetic, therapeutically or prophylactically active, peptide fragments, peptide analogues, and chemically modified derivatives or salts of active peptides. A variety of peptide analogues and derivatives are available and others can be contemplated for use within the invention and can be produced and tested for biological activity according to known methods. Peptides for use within the invention can be peptides that are obtainable by partial substitution, addition, or deletion of amino acids within a naturally occurring or native peptide sequence. Peptides can be chemically modified, for example, by amidation of the carboxyl terminus ($—NR_2$), the use of D amino acids in the peptide, incorporation of small non-peptidyl moieties, as well as the modification of the amino acids themselves (e.g. alkylation or esterification of side chain R-groups). Such analogues, derivatives and fragments should substantially retain or enhance the desired biological activity of the native peptide.

All peptides described and/or contemplated herein can be prepared by chemical synthesis using either automated or manual solid phase synthetic technologies, generally known in the art. The peptides can also be prepared recombinantly, using techniques known in the art.

A list of peptides is included in Table I, however one skilled in the art would know this list is not complete and one could contemplate and produce additional peptides, analogues and derivatives. Enkephalin was isolated from mammalian brains and found to be a mixture of two pentapeptides which differ only in the amino acid present at the 5-position. The two pentapeptides are methionine enkephalin (also known as met-enk or met-enkephalin) and leucine enkephalin (also known as leu-enk or leu-enkephalin). Met-enkephalin has an amino acid sequence of Tyr-Gly-Gly-Phe-Met and leu-enkephalin has an amino acid sequence of Tyr-Gly-Gly-Phe-Leu wherein the Tyr, Met and Leu residues are all L-amino acids. The tyrosine moiety is important for activity and probably corresponds to the 3-hydroxyl group on the morphine molecule. Proenkephalin A is the precursor for met-enkephalin, leu-enkephalin and several other larger peptides. The structure of proenkephalin A contains four copies of met-enkephalin and one copy of leu-enkephalin, along with a heptapeptide (met-enk-Arg-Phe) and an octapeptide (met-enk-Arg-Gly-Leu). A series of peptides containing met-enkephalin at the N-terminus also possess opioid activity, and include peptide F and peptide E. Peptide F contains two met-enkephalin sequences one at each end, while peptide E contains met-enkephalin at the N-terminus and leu-enkephalin at the C-terminus.

In addition to naturally occurring enkephalins, enkephalin analogues and derivatives are known in the art, including, for example, derivatives and analogues which are specific for different types of opiate receptors. (Hruby and Gehrig (1989) *Medicinal Research Reviews* 9:343-401). Furthermore, enkephalin peptides can be modified by replacement and/or modification of specific amino acids, as it is known in the art that these modifications decrease the rate of hydrolysis and degradation of enkephalins by proteases.

β-endorphin is a 31-amino acid peptide formed from a larger precursor, pro-opiomelanocortin. β-endorphin contains a tetrapeptide sequence (Tyr-Gly-Gly-Phe) which is common to the enkephalin peptides and this tetrapeptide sequence appears to be essential to the function of these peptides. α-endorphin is a 16-amino acid peptide that is also formed from precursor pro-opiomelanocortin.

Dynorphins are another class of endogenous opioids that exist in multiple forms in the central nervous system. Dynorphins derive from precursor prodynorphin (proenkephalin B). Dynorphin, also known as Dynorphin A1-17, is a well-known opioid peptide that has the sequence Tyr-Gly-Gly-Phe-Leu-Arg-Arg-Ile-Arg-Pro-Lys-Leu-Lys-Trp-Asp-Asn-Gln. Smaller peptides such as dynorphin A1-8 and three leu-enkephalins are also contained within proenkephalin B and are abundant in the neural lobe of the pituitary gland. Dynorphin A1-13 has been found in the striatonigral pathway and may provide a feedback mechanism for regulating dopaminergic activity in the striatum.

Endomorphins are amidated tetrapeptides and are structurally unrelated to the other endogenous opioid peptides. Two peptides, endomorphin-1 and endomorphin-2 have been isolated from mammalian brain. Both peptides have similar characteristics including analgesia against heat stimuli, mechanical stimuli and inflammatory and neuropathic pain. (Zadina et al. (1997) *Nature* 386:499-502; Hackler et al. (1997) *Peptides* 18:1635-1639)

Casomorphin peptides are novel opioid peptides derived from casein. Beta-casomorphins are the more extensively studied opioid peptides arising from the proteolytic breakdown of food proteins. The β-casomorphin peptide, Tyr-Pro-Phe-Pro-Gly-Pro-Ile was originally isolated from bovine beta-casein, and subsequently peptides with the same sequence were identified originating from ovine and buffalo beta-caseins. A human beta-casomorphin has been identified and has two amino acid differences from the bovine sequence, Tyr-Pro-Phe-Val-Glu-Pro-Ile. Several other casomorphin peptides have been isolated including β-casomorphin 1-3, β-casomorphin 1-4, β-casomorphin 1-5 and β-casomorphin 1-8.

Dermorphin is a seven amino acid peptide, originally isolated from *Phylomedusa sauvagei* frog skin. It is a ligand which binds with high affinity to the mu opioid receptor and has many biological roles including analgesia, endocrine modulation, immunomodulation, increased K+ conductance and inhibition of action potentials.

Oxytocin is a nine amino acid cyclic peptide hormone that is released from the posterior lobe of the pituitary gland and stimulates the contraction of smooth muscle of the uterus during labor and facilitates release of milk from the breast during nursing. Studies have shown that oxytocin can also play an important role in nociceptive modulation. The mu receptors as well as oxytocin receptors appear to be the predominant receptor bound by oxytocin and that they both are involved in oxytocin's physiological effects. (Wang et al. (2003) *Regul. Pept.*, 115:153-159; Zubrzycka et al. (2005) *Brain Res.* 1035:67-72).

Accordingly, in some aspects of the invention, the analgesic agent can be an opioid peptide selected from the group comprising leu-enkephalin, met-enkephalin, met-enk-Arg-Phe, met-enk-Arg-Gly-Leu, peptide E, peptide F, β-endorphin, α-endorphin, dynorphin A1-17, dynorphin B, beta-neoendorphin, α-neoendorphin, dynorphin A1-8, dynorphin A 1-13, endomorphin-1, endomorphin-2, β-casomorphin, β-casomorphin 1-3, β-casomorphin 1-4, β-casomorphin 1-5, β-casomorphin 1-8, dermorphin, deltorphin I, deltorphin II, dermenkephalin, morphiceptin, oxytocin and analogues and derivatives thereof. In some examples more than one peptide is administered. In other examples, an opioid peptide is administered in combination with a second agent. In some examples, the opioid peptide is administered in combination with more than one additional agent.

TABLE I

| Name | Amino Acid Sequence | |
|---|---|---|
| Leu-enkephalin | Tyr-Gly-Gly-Phe-Leu | SEQ ID NO: 1 |
| Met-enkephalin | Tyr-Gly-Gly-Phe-Met | SEQ ID NO: 2 |
| Peptide F | Tyr-Gly-Gly-Phe-Met-Lys-Lys-Met-Asp-Glu-Leu-Tyr-Pro-Leu-Glu-Val-Glu-Glu-Glu-Ala-Asn-Gly-Gly-Phe-Val-Leu-Gly-Lys-Arg-Try-Gly-Gly-Phe-Met | SEQ ID NO: 3 |
| β-endorphin (human) GenBank 764134 | Tyr-Gly-Gly-Phe-Met-Thr-Ser-Glu-Lys-Ser-Gln-Thr-Pro-Leu-Val-Thr-Leu-Phe-Lys-Asn-Ala-Ile-Ile-Lys-Asn-Ala-Tyr-Lys-Lys-Gly-Glu | SEQ ID NO: 4 |
| α-endorphin | Tyr-Gly-Gly-Phe-Met-Thr-Ser-Glu-Ser-Gln-Thr-Pro-Leu-Val-Thr-NH$_2$ | SEQ ID NO: 5 |
| Dynorphin A | Tyr-Gly-Gly-Phe-Leu-Arg-Arg-Ile-Arg-Pro-Lys-Leu-Lys-Trp-Asp-Asn-Gln | SEQ ID NO: 6 |
| Dynorphin B | Tyr-Gly-Gly-Phe-Leu-Arg-Arg-Gln-Phe-Lys-Val-Val-Thr | SEQ ID NO: 7 |
| α-neoendorphin | Tyr-Gly-Gly-Phe-Leu-Arg-Lys-Tyr-Pro-Lys | SEQ ID NO: 8 |
| β-neoendorphin | Tyr-Gly-Gly-Phe-Leu-Arg-Lys-Tyr-Pro | SEQ ID NO: 9 |
| Dynorphin A1-8 | Tyr-Gly-Gly-Phe-Leu-Arg-Arg-Ile | SEQ ID NO: 10 |
| Dynorphin A1-13 | Tyr-Gly-Gly-Phe-Leu-Arg-Arg-Ile-Arg-Pro-Lys-Leu-Lys | SEQ ID NO: 11 |
| Endomorphin-1 | Tyr-Pro-Trp-Phe-NH$_2$ | SEQ ID NO: 12 |
| Endomorphin-2 | Tyr-Pro-Phe-Phe-NH$_2$ | SEQ ID NO: 13 |

TABLE I-continued

| Name | Amino Acid Sequence | |
|---|---|---|
| Dermorphin | Tyr-(D)Ala-Phe-Gly-Tyr-Pro-Ser-NH$_2$ | SEQ ID NO: 14 |
| β-casomorphin (bovine) | Tyr-Pro-Phe-Pro-Gly-Pro-Ile | SEQ ID NO: 15 |
| β-casomorphin (human) | Tyr-Pro-Phe-Val-Glu-Pro-Ile | SEQ ID NO: 16 |
| β-Casomorphin 1-3 | Tyr-Pro-Phe | SEQ ID NO: 17 |
| β-Casomorphin 1-4 | Tyr-Pro-Phe-Pro | SEQ ID NO: 18 |
| β-Casomorphin 1-4, amide | Tyr-Pro-Phe-Pro-NH$_2$ | SEQ ID NO: 19 |
| β-casomorphin 1-5 | Tyr-Pro-Phe-Pro-Gly | SEQ ID NO: 20 |
| β-Casomorphin 1-8 | Tyr-Pro-Phe-Pro-Gly-Pro-Ile-Pro | SEQ ID NO: 21 |
| Deltorphin I | Tyr-(D)Ala-Phe-Asp-Val-Val-Gly-NH$_2$ | SEQ ID NO: 22 |
| Deltorphin II | Tyr-(D)Ala-Phe-Glu-Val-Val-Gly-NH$_2$ | SEQ ID NO: 23 |
| Dermenkephalin | Tyr-(D)Met-Phe-His-Leu-Met-Asp-NH$_2$ | SEQ ID NO: 24 |
| Dermorphin | Tyr-(D)Ala-Phe-Gly-Tyr-Pro-Ser | SEQ ID NO: 25 |
| Morphiceptin | Tyr-Pro-Phe-Pro-NH$_2$ | SEQ ID NO: 26 |
| Oxytocin | Cys-Tyr-Ile-Gln-Asn-Cys-Pro-Leu-Gly | SEQ ID NO: 27 |

Other analgesic or potentially analgesic agents can include opioids, amino acids, non-opioid peptides, polypeptides, non-peptidic compounds and small molecule compounds. These agents may have an analgesic effect by interacting with opiate receptors, non-opiate receptors and/or ion channels. These agents can include, but are not limited to, peptidergic channel modulators, peptidergic enzyme inhibitors, analgesic enzymes, trophic factors, peptidergic receptor agonists, peptidergic receptor antagonists, amino acid receptor agonists, N-methyl-D-aspartate receptor blockers, nicotinic agonists, non-steroidal anti-inflammatory drugs (NSAIDs), steroid anti-inflammatory drugs, ion channel blockers, antidepressants, anti-seizure medications, antibodies directed toward proalgesic antigens and antibodies directed to other neuropeptides. Channel modulators may include snail toxins, such as omega-conotoxin MVIIA, and their derivatives, saxitoxin and tetrodotoxin. Enzyme inhibitors may include cyclosporin A, bestatin, bestatin analogue Z4212 (N-[(2S, 3R)-3-Amino-2-hydroxy-4-(4-3. methylsulphonyl-phenyl)-1-oxobutyl]-1-aminocyclopentanecarboxylic) and bestatin analogue Z 1796 ((2S)—N-[(2S,3R)-3-Amino-2-hydroxy-4-(4-methylsulphonyl-phenyl)-1-oxobutyl]-L-leucine). Analgesic enzymes may include endothelin-1 peptidase. Trophic factors may include glial-derived neurotrophic factor (GDNF) and brain-derived neurotrophic factor (BDNF). Peptidergic receptor agonists may include somatostatin and its synthetic analogue octreotide, nocistatin, galanin and neuropeptide Y. Peptidergic receptor antagonists may include calcitonin gene-related peptide receptor antagonist CGRP(8-37), cholecystokinin (CCK) receptor antagonists such as Tyr-(D)Phe-Gly-(D)Trp-NMeNle-Asp-Phe-NH$_2$ or PD134308, neurokinin-1 receptor (substance P receptor) antagonists such as spantide II ((D)-NicLys1, 3-Pal3, D-Cl2Phe5, Asn6, D-Trp7,9, Nle11-substance P), vasoactive intestinal peptide (VIP) receptor antagonists such as (Ac-Try1, D-Phe2)-GRF-(1-29) (where GRF is growth hormone releasing factor) and galanin receptor antagonists such as RWJ-57408). Amino acid receptor agonists may include gamma-amino butyric acid (GABA) and glycine. N-methyl-D-asparate (NMDA) receptor blockers may include ketamine and dextromethorphan. Anti-seizure medications that decrease pain may include gabapentin, lamotrigine, tiagabine, topiramate, carbamazepine, oxcarbazepine, clonazepam, valproic acid, and phenyloin. Nicotinic agonists may include nicotine and epibatidine. Typical and atypical non-steroidal anti-inflammatory drugs may include aspirin, acetaminophen, choline and magnesium salicylates, choline salicylate, celecoxib, diclofenac potassium, diclofenac sodium, diclofenac sodium with misoprostol, diflunisal, etodolac, fenoprofen calcium, flurbiprofen, ibuprofen, indomethacin, ketorolac, ketoprofen, magnesium salicylate, meclofenamate sodium, mefenamic acid, meloxicam, nabumetone, naproxen, naproxen sodium, oxaprozin, piroxicam, rofecoxib, salsalate, sodium salicylate, sulindac, tolmetin sodium, valdecoxib. Steroid anti-inflammatory drugs may include prednisone and dexamethasone. Ion channel blockers may include selective blockers of TrpV1, TrpV2, Nav1.3, Nav1.7, Nav1.8, Nav1.9 and ASICs (acid sensing ion channels), as well as P, Q, and N type calcium channels, such as ziconotide, and non-specific sodium channel blockers, such as mexiletine, lidocaine, cocaine, mepivacaine, prilocaine, bupivacaine and eidocaine. Antidepressants may include amitriptyline, nortryptiline, desipramine, paroxetine, citralopram, venlafaxine, clomipramine, and bupropion. Antibodies directed toward proalgesic antigens may include antibodies to endothelin, nerve growth factor, vasoactive intestinal peptide (VIP) and pituitary adenylate cyclase-activating polypeptide (PACAP). Antibodies directed toward other neuropeptides may include antibodies to CGRP, CCK, substance P and galanin. Other compounds may include, but are not limited to, SNC 80, DPI-125, clonidine, dexmedetomidine, calcitonin, baclofen, d-cycloserine, ergotamine, serotonin agonists and 5HT drugs. One skilled in the art would know this list is not complete and it is believed that one could contemplate and produce additional peptides, polypeptides, non-peptidic compounds, small molecule compounds, analogues and derivatives thereof which have analgesic properties.

Accordingly, in some aspects of the invention, the analgesic agent is an amino acid, a non-opioid peptide, a polypeptide, a non-peptidic compound or a small molecule compound. In some examples, two agents are administered in combination. In other examples, more than two agents are administered in combination. The agents may be administered at the same time or may be administered at different times.

Administration

Chronic, acute or procedural pain associated with the trigeminal nerve system is experienced in many syndromes and diseases including, but not limited to, trigeminal neuralgia, atypical facial pain, anesthesia dolorosa, post-herpetic neuralgia, cancer of the head and neck, migraine headaches, other types of headaches, temporomandibular joint pain, injuries to the face and/or head, injuries or infections of the teeth, common dental procedures and facial surgeries such as cosmetic plastic surgery. It is believed that analgesic agents can be targeted to the trigeminal nerve system and that this directed administration can result in analgesia and pain relief for a individual suffering acute, chronic or procedural facial or head pain.

The trigeminal nerve (fifth cranial nerve or CN V) is the largest of the 12 cranial nerves and it is the principal general sensory nerve to the head, particularly the face and is the motor nerve to the muscles of mastication. The trigeminal nerve innervates tissues of a mammal's (e.g. human) head including skin of the face and scalp, oral tissues and tissues of and surrounding the eye. The trigeminal nerve has three major branches or divisions: the ophthalmic, the maxillary, and the mandibular divisions. Thus, some aspects of the present invention include methods for treating an individual for trigeminal nerve-associated pain comprising administering to the individual an analgesic agent wherein the administration of the analgesic agent is targeted to one or more of the three major branches of the trigeminal nerve including the ophthalmic, maxillary, and mandibular divisions.

The ophthalmic division is the superior division of the trigeminal nerve, it is the smallest of the three branches and is wholly sensory. The ophthalmic nerve has three branches known as the nasociliary nerve, the frontal nerve, and the lacrimal nerve which participate in the sensory supply to the skin of the forehead, upper eyelid and nose. The nasociliary nerve further divides into the anterior ethmoidal nerve and the infratrochlear nerve, while the frontal nerve divides into the supratrochlear and supraorbital nerves. The supratrochlear nerve supplies the middle part of the forehead, and the supraorbital nerve supplies the lateral part and the front of the scalp. The lacrimal nerve, supplies the lacrimal gland and the lateral part of the upper eyelid. Thus, in some aspects, methods of the invention involve administration of an analgesic agent to the one or more of the nerves branching from the ophthalmic nerve including the nasociliary nerve, frontal nerve, lacrimal nerve, anterior ethmoidal nerve, infratrochlear nerve, supratrochlear nerve and supraorbital nerve.

The maxillary division is the intermediate division of the trigeminal nerve. It has three cutaneous branches: the infraorbital nerve which participates in the sensory supply to the skin on the lateral aspect of the nose, upper lip, and lower eyelid; the zygomaticofacial nerve, which supplies the skin of the face over the zygomatic bone; and the zygomaticotemporal nerve which supplies the skin over the temporal region. Thus, in some aspects, methods of the invention involve administration of an analgesic agent to the one or more of the nerves branching from the maxillary nerve including infraorbital, zygomaticofacial and zygomaticotemporal.

The mandibular division is the inferior division of the trigeminal nerve. It has three sensory branches: the buccal nerve supplies the skin of the cheek over the buccinator muscle. It also supplies the mucous membrane lining of the cheek and the posterior part of the buccal surface of the gingiva (gum). The auriculotemporal nerve supplies parts of the auricle, the external acoustic meatus, the tympanic membrane (eardrum) and the skin in the temporal region. The inferior alveolar nerve further divides into the incisive nerve and the mental nerve. The incisive nerve supplies the incisor teeth, the adjacent gingiva, and the mucosa of the lower lip and the mental nerve supplies the skin of the chin, the skin and mucosa membrane of the lower lip and gingiva. The lingual nerve supplies general sensory fibers to the anterior two-thirds of the tongue, the floor of the mouth, and the gingiva of the mandibular teeth. Thus, in some aspects, methods of the invention involve administration of an analgesic agent to one or more of the nerves branching from the mandibular nerve including buccal, auriculotemporal, inferior alveolar, incisive, mental and lingual.

Accordingly, some aspects of the invention include methods for treating an individual for trigeminal nerve-associated pain comprising administering to the individual an analgesic agent to mucosa tissue or epithelium within the oral cavity, within or around the eye or to the skin. The methods can include administering an agent to oral tissues wherein the analgesic agent is targeted to mucosal tissue innervated by a trigeminal division, for example the mandibular division. The oral mucosal tissues include, but are not limited to, the gingiva (gums), the floor of the oral cavity, the cheeks, the lips, the tongue, the teeth or a combination thereof. The methods can include administering an agent to conjunctiva or other mucosal tissues around the eye wherein the analgesic agent is targeted to mucosal tissue or epithelium innervated by a trigeminal division, for example the ophthalmic or maxillary division. The tissues or epithelium include, but are not limited to, the conjunctiva, the lacrimal gland, the nasolacrimal ducts, the mucosa of the upper or lower eyelid, the eye, or a combination thereof. An agent that is administered to the conjunctiva but not absorbed completely through the conjunctival mucosa can drain through the nasolacrimal ducts into the nose wherein it can be absorbed by mucosal tissue innervated by the trigeminal nerve within the nasal cavity. The methods can include administering an agent to skin of the face or head wherein the analgesic agent is targeted to tissue innervated by one of the trigeminal divisions. The agent can be administered to the skin of the face, scalp or temporal region. Suitable skin of the face includes skin of the chin, the upper lip, the lower lip, the forehead, the nose, the cheek, the skin around the eyes, the upper eyelid, the lower eyelid or combinations thereof. Suitable skin of the scalp includes the front of the scalp, the scalp over the temporal region, the lateral part of the scalp, or combinations thereof. Suitable skin of the temporal region includes the temple and the scalp over the temporal region and combinations thereof.

Within the nasal cavity, the trigeminal nerve innervates mainly the inferior two-thirds of the nasal mucosa, while the olfactory nerve innervates the superior upper third of the nasal mucosa. There are primary afferent somotosensory neuronal fibers in the trigeminal nerve which allows for craniofacial somatosensory information including touch, temperature, proprioception (position sense) and pain. Those that are involved in pain (nociception) are termed "nociceptors". In contrast, there are no nociceptors or other somatosensory primary afferents in the olfactory nerve which is essentially devoted to the sense of smell and pheromone detection. The anterior ethmoidal nerve, a branch of the nasociliary nerve, innervates, among other tissues, the ethmoidal sinus and regions of the inferior two-thirds of the nasal mucosa, including the anterior portion of the nasal septum and the lateral wall of the nasal cavity. The maxillary division has several branches that innervate the nasal cavity and sinuses, including the nasopalatine nerve, the greater palatine nerve, the posterior superior alveolar nerves, the middle superior alveolar nerve and the anterior superior alveolar nerve. The maxillary sinus is innervated by the posterior, middle and anterior superior alveolar nerves. The mucous membrane of the nasal septum is supplied chiefly by the nasopalatine nerve and the lateral wall of the nasal cavity is supplied by the greater palatine nerve.

Accordingly, some aspects of the invention include methods for treating an individual for trigeminal nerve-associated pain comprising administering to the individual an analgesic agent to mucosa tissue within the nasal cavity. In some examples, the methods include administration of an analgesic agent to the inferior two-thirds of the nasal cavity wherein the analgesic agent is targeted to mucosal tissue innervated by the trigeminal nerve and away from the olfactory nerve. In some examples, the methods include administration of an analgesic agent to the inferior two-thirds of the nasal cavity wherein the analgesic agent preferentially binds to opioid receptors within the trigeminal nerves. In some examples, the methods also include administration of an analgesic agent to the inferior two-thirds of the nasal cavity wherein the analgesic agent preferentially binds to non-opioid receptors within the trigeminal nerve system. Thus, in some aspects of the invention, methods involve administration of an analgesic agent to one or more of the nerves branching from the maxillary division that innervate the nasal cavity including nasopalatine, greater palatine, posterior superior alveolar, middle superior alveolar and anterior superior alveolar.

Intranasal drug delivery has been a topic of research and development for many years, although it has been only within the past decade that carrier systems have been devised which make delivery of substances effective. (Sayani and Chien (1996) *Critical Reviews in Therapeutic Drug Carrier Systems,* 13:85-184.)

Intranasal delivery of analgesic agents has a number of advantageous features including comparatively high bioavailability, rapid kinetics of absorption and avoidance of liver first-pass effect. In regard to patient compliance and ease of use, intranasal administration provides a simple, rapid and non-invasive mode of application. In particular, intranasal delivery can allow for targeted delivery of an analgesic agent to the nasal cavity and to the trigeminal nerve system to treat or prevent trigeminal nerve-associated pain. Furthermore, targeted delivery to the trigeminal nerve system and preferably not the olfactory region can reduce the amount of drug entering the CNS or systemic circulation thereby reducing or eliminating CNS effects or systemic side effects. Targeted delivery to the trigeminal nerve system can reduce the effective dosage necessary to achieve analgesia in the facial or head regions wherein lower effective dosages will further reduce CNS or systemic side effects.

Accordingly, some aspects of the present invention include methods for treating an individual for trigeminal nerve-associated pain comprising administering to the individual an analgesic agent by intranasal administration wherein the administration is targeted to the trigeminal nerve system and results predominantly in analgesia to the facial or head region, particularly as compared to analgesic effects in other parts of the body. The methods can administer an analgesic agent to the nasal cavity of an individual, in particular to the inferior two-thirds of the nasal cavity, to promote delivery to the trigeminal nerve system with minimal delivery to the olfactory nerve.

Within the oral cavity, the buccal or sublingual delivery routes are convenient choices for drug delivery as they are user-friendly and non-invasive. Some of the advantages include i) less proteolytic activity in the oral cavity as compared to some other routes thereby avoiding the problems of enzymatic degradation of peptide and protein drugs and ii) bypassing the liver first pass effect. In particular, buccal or sublingual delivery can allow for targeted delivery of an analgesic agent to the oral mucosa and to the trigeminal divisions that innervate the oral mucosa to treat or prevent trigeminal nerve-associated pain. Targeted delivery to a trigeminal division can reduce the effective dosage necessary to achieve analgesia in the facial or head regions wherein lower effective dosages will further reduce CNS effects or systemic side effects.

Accordingly, some aspects of the present invention include methods for treating an individual for trigeminal nerve-associated pain comprising administering to the individual an analgesic agent by buccal or sublingual administration wherein the administration is targeted to a trigeminal division and results predominantly in analgesia to the facial or head region. The methods involve administration of an analgesic agent to the oral cavity of an individual to promote delivery to the trigeminal nerve with minimal systemic distribution.

Drug delivery to the mucosal tissue around the eye or to the conjunctiva is another convenient choice for drug delivery that is non-invasive. In particular, administration to the mucosa or epithelium of the eyelids, the conjunctiva or the lacrimal system can allow for targeted delivery of an analgesic agent to the mucosa and tissues innervated by trigeminal divisions to treat or prevent trigeminal nerve-associated pain. Targeted delivery to a trigeminal division can reduce the effective dosage necessary to achieve analgesia in the facial or head regions wherein lower effective dosages will further reduce CNS effects or systemic side effects.

Accordingly, some aspects of the present invention include methods for treating an individual for trigeminal nerve-associated pain comprising administering to the individual an effective amount of an analgesic agent to the conjunctiva or other mucosal tissues around the eye wherein the administration is targeted to a trigeminal division and results predominantly in analgesia to the facial or head region.

Transdermal drug delivery or administration of a therapeutic agent to the skin has become a proven technology over the last 20 years. Transdermal drug delivery offers controlled release of a drug to the patient and transdermal patches are user-friendly, convenient, painless, and offer multi-day dosing which usually results in improved patient compliance. Administration to the skin by transdermal delivery can allow for targeted delivery of an analgesic agent to the skin innervated by any one of the trigeminal divisions or a combination thereof to treat or prevent trigeminal nerve-associated pain in the facial or head regions.

Accordingly, some aspects of the present invention include methods for treating an individual for trigeminal nerve-associated pain comprising administering to the individual an effective amount of an analgesic agent to the skin of the face, head or scalp wherein the administration is targeted to the trigeminal nerve system and results predominantly in analgesia to the facial or head region. In some examples, the analgesic agent is administered to particular sites on the face or scalp to promote delivery to particular trigeminal divisions.

In some aspects of the invention a vasoconstrictor is used to decrease systemic distribution of the analgesic agent. The vasoconstrictor can be included in a pharmaceutical composition to decrease systemic distribution of the analgesic agent. Alternatively, the vasoconstrictor may be delivered to the mucosal or dermal surface separately from the pharmaceutical composition. Vasoconstrictors are compounds that constrict blood vessels and capillaries and decrease blood flow. They can be used to increase concentration of an agent at a desired site by inhibiting movement of the analgesic agent into the bloodstream and thereby reducing systemic distribution of the agent Vasoconstrictors can be used to decrease the effective dosage of agent needed to achieve analgesia by limiting systemic distribution and concentrating the agent in the trigeminal nerve. A vasoconstrictor can be administered before administration of the analgesic agent or can be co-administered with the analgesic agent. Vasoconstrictors may include, but are not limited to, phenylephrine hydrochloride, tetrahydrozoline hydrochloride, naphazoline nitrate, oxymetazoline hydrochloride, tramazoline hydrochloride, endothelin-1, endothelin-2, epinephrine, norepinephrine and angiotensin.

In some examples of the invention, methods involve administration of a vasoconstrictor to the oral cavity of an individual prior to administration of an analgesic agent to the oral cavity, wherein administration of the vasoconstrictor decreases systemic distribution of the analgesic agent thereby minimizing undesirable CNS effects or systemic side effects. In other examples, methods involve administration of a vasoconstrictor and an analgesic agent to the oral cavity of an individual. A vasoconstrictor may be administered to the oral cavity of an individual prior to or at the same time as an analgesic agent, wherein administration of the vasoconstrictor decreases systemic distribution of the analgesic agent thereby decreasing the effective dosage amount of analgesic agent necessary to achieve analgesia to the facial or head region.

In some examples of the invention, methods involve administration of a vasoconstrictor to the nasal cavity of an individual prior to administration of an analgesic agent to the nasal cavity, wherein administration of the vasoconstrictor decreases systemic distribution of the analgesic agent thereby minimizing undesirable CNS effects or systemic side effects. The methods can co-administer a vasoconstrictor and an analgesic agent to the nasal cavity of an individual, wherein administration of the vasoconstrictor decreases systemic distribution of the analgesic agent thereby minimizing undesirable CNS or systemic side effects. The methods can administer a vasoconstrictor to the nasal cavity of an individual prior to or co-administer with an analgesic agent, wherein administration of the vasoconstrictor decreases systemic distribution of the analgesic agent thereby decreasing the effective dosage amount of analgesic agent necessary to achieve analgesia to the facial or head region.

Pharmaceutical Composition

While it is possible to administer an analgesic agent alone, there are situations wherein it is advantageous to present it as part of a pharmaceutical composition. Thus, in some aspects of the present invention, the analgesic agent is administered as a pharmaceutical composition. The pharmaceutical composition can comprise an analgesic agent at a therapeutically effective dose together with one or more pharmaceutically acceptable carriers and optionally other ingredients. A suitable carrier is one which does not cause an intolerable side effect, but which allows the analgesic agent to retain its pharmacological activity in the body. A carrier may also reduce any undesirable side effects of the agent. A suitable carrier should be stable, i.e., incapable of reacting with other ingredients in the formulation. A suitable carrier should have minimal odor or fragrance or fragrance or a positive (pleasant) odor. A suitable carrier should not irritate the mucosa, epithelium, underlying nerves or provide a health risk. It may be an accepted transcutaneous or percutaneous carrier or vehicle, because any carrier that can effectively penetrate the stratum corneum of the skin should be highly efficacious in not only penetrating mucosa, but also allowing rapid absorption of substances into the submucosal tissues, nerve sheaths and nerves.

Suitable nontoxic pharmaceutically acceptable carriers will be apparent to those skilled in the art of pharmaceutical formulations. Also see *Remington: The Science and Practice of Pharmacy,* 20th Edition, Lippincott, Williams & Wilkins (2000). Typical pharmaceutically acceptable carriers include, but are not limited to, mannitol, urea, dextrans, lactose, potato and maize starches, magnesium stearate, talc, vegetable oils, polyalkylene glycols, ethyl cellulose, poly(vinylpyrrolidone), calcium carbonate, chitosan, ethyl oleate, isopropyl myristate, benzyl benzoate, sodium carbonate, gelatin, potassium carbonate, silicic acid, and other conventionally employed acceptable carriers. Other carriers include, but are not limited to, phosphatidylcholine, phosphatidylserine, and sphingomyelins.

The choice of a suitable carrier will depend on the exact nature of the particular formulation desired, e.g., whether the drug is to be formulated into a liquid solution (e.g., for use as drops, as a spray or impregnated in a nasal tampon, or other agent-impregnated solid), a suspension, a ointment or a gel. If desired, sustained-release compositions, e.g. sustained-release gels, transdermal patches, etc. can be readily prepared. The particular formulation will also depend on the route of administration. The agent can be administered to the nasal cavity as a powder, a granule, a solution, a film, a cream, a spray, a gel, an ointment, an infusion, a drop or a sustained-release composition. For buccal administration, the composition can take the form of tablets or lozenges formulated in a convention manner. For sublingual administration, the composition can take the form of a bioadhesive, a spray, paint or a swab applied to or under the tongue. For administration to the conjunctiva or other mucosal tissues around the eye, the composition can be applied as an ointment, a solution or a drop. For administration to the skin, the composition can be applied as a topical ointment, a topical gel, a cream, a lotion, a solution, a spray, a paint, a film, a foil, a cosmetic, a patch or a bioadhesive.

Liquid carriers include, but are not limited to, water, saline, aqueous dextrose, and glycols particularly (when isotonic) for solutions. The carrier can be also be selected from various oils, including those of petroleum, animal, vegetable or synthetic origin, (e.g. peanut oil, soybean oil, mineral oil, sesame oil, and the like). Suitable pharmaceutical excipients include, but are not limited to, starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol, and the like. The compositions can be subjected to conventional pharmaceutical expedients, such as sterilization, and can contain conventional pharmaceutical additives, such as preservatives, stabilizing agents, reducing agents, anti-oxidants, chelating agents, wetting agents, emulsifying agents, dispersing agents, jelling agents, salts for adjusting osmotic pressure, buffers, and the like. Where the carrier is a liquid, it is preferred that the carrier be hypotonic or isotonic with body fluids and have a pH within the range of 4.5-8.5. Where the carrier is in powdered form, it is preferred that the carrier be within an acceptable non-toxic pH range. The use of additives in the preparation of peptide and/or protein-based compositions, particularly pharmaceutical compositions, is well-known in the art.

These lists of carriers and additives are by no means complete and a worker skilled in the art can choose excipients from the GRAS (generally regarded as safe) list of chemicals allowed in the pharmaceutical preparations and those that are currently allowed in topical and parenteral formulations. (See also Wang et al., (1980) *J. Parent. Drug Assn.*, 34:452-462; Wang et al., (1988) *J. Parent. Sci. and Tech.*, 42:S4-S26.)

Other forms of compositions for administration include a suspension of a particulate, such as an emulsion, a liposome, or in a sustained-release form to prolong the presence of the pharmaceutically active agent in an individual. The powder or granular forms of the pharmaceutical composition may be combined with a solution and with a diluting, dispersing or surface-active agent. Additional compositions for administration include a bioadhesive to retain the agent at the site of administration, for example a spray, paint, or swab applied to the mucosa or epithelium. A bioadhesive can refer to hydrophilic polymers, natural or synthetic, which, by the hydrophilic designation, can be either water soluble or swellable and which are compatible with the pharmaceutical composition. Such adhesives function for adhering the formulations to the mucosal tissues of the oral or nasal cavity. Such adhesives can include, but are not limited to, hydroxypropyl cellulose, hydroxypropyl methylcellulose, hydroxy ethylcellulose, ethylcellulose, carboxymethyl cellulose, dextran, gaur gum, polyvinyl pyrrolidone, pectins, starches, gelatin, casein, acrylic acid polymers, polymers of acrylic acid esters, acrylic acid copolymers, vinyl polymers, vinyl copolymers, polymers of vinyl alcohols, alkoxy polymers, polyethylene oxide polymers, polyethers, and combinations thereof. The composition can also be in the form of lyophilized powder, which can be converted into solution, suspension, or emulsion before administration. The pharmaceutical composition is preferably sterilized by membrane filtration and is stored in unit-dose or multi-dose containers such as sealed vials or ampoules.

The pharmaceutical composition can be formulated in a sustained-release form to prolong the presence of the active agent in the treated individual. Many methods of preparation of a sustained-release formulation are known in the art and are disclosed in *Remington's Pharmaceutical Sciences* (see above). Generally, the agent can be entrapped in semi-permeable matrices of solid hydrophobic polymers. The matrices can be shaped into films or microcapsules. Matrices can include, but are not limited to, polyesters, co-polymers of L-glutamic acid and gamma ethyl-L-glutamate, polylactides, polylactate polyglycolate, hydrogels, non-degradable ethylene-vinyl acetate, degradable lactic acid-glycolic acid copolymers, hyaluronic acid gels, and alginic acid suspensions. Suitable microcapsules can also include hydroxymethylcellulose or gelatin and poly-methyl methacrylate. Microemulsions or colloidal drug delivery systems such as liposomes and albumin microspheres can also be used. Some sustained-release compositions can use a bioadhesive to retain the agent at the site of administration.

To further enhance the mucosal delivery of a pharmaceutical composition comprising an analgesic agent, an enzyme inhibitor, particularly proteases inhibitors, can be included in the formulation. Protease inhibitors may include, but are not limited to, antipain, arphamenine A and B, benzamidine HCl, AEBSF, CA-074, calpain inhibitor I and II, calpeptin, pepstatin A, actinonin, amastatin, bestatin, boroleucine, captopril, chloroacetyl-HOLeu-Ala-Gly-NH2, DAPT, diprotin A and B, ebelactone A and B, foroxymithine, leupeptin, pepstatin A, phosphoramidon, aprotinin, puromycin, BBI, soybean trypsin inhibitor, phenylmethylsulfonyl fluoride, E-64, chymostatin, 1,10-phenanthroline, EDTA and EGTA.

To enhance delivery into or across a mucosal surface and/or absorption of a pharmaceutical composition comprising an analgesic agent, an absorption-enhancing agent can be included in the formulation. These enhancing agents may enhance the release or solubility (e.g., from a formulation delivery vehicle), diffusion rate, penetration capacity and timing, uptake, residence time, stability, effective half-life, peak or sustained concentration levels, clearance and other desired mucosal delivery characteristics (e.g., as measured at the site of delivery) of the composition. Enhancement of mucosal delivery can thus occur by any of a variety of mechanisms, for example by increasing the diffusion, transport, persistence or stability of an analgesic agent, increasing membrane fluidity, modulating the availability or action of calcium and other ions that regulate intracellular or paracellular permeation, solubilizing mucosal membrane components (e.g., lipids), changing non-protein and protein sulfhydryl levels in mucosal tissues, increasing water flux across the mucosal surface, modulating epithelial junctional physiology, reducing the viscosity of mucus overlying the mucosal epithelium, reducing mucociliary clearance rates, and other mechanisms.

Mucosal absorption enhancing compounds may include, but are not limited to, surfactants, bile salts, dihydrofusidates, bioadhesive agents, phospholipid additives, mixed micelles, liposomes, or carriers, alcohols, enamines, cationic polymers, NO donor compounds, long-chain amphipathic molecules, small hydrophobic penetration enhancers; sodium or a salicylic acid derivatives, glycerol esters of acetoacetic acid, cyclodextrin or beta-cyclodextrin derivatives, medium-chain fatty acids, chelating agents, amino acids or salts thereof, N-acetylamino acids or salts thereof, mucolytic agents, enzymes specifically targeted to a selected membrane component, inhibitors of fatty acid synthesis and inhibitors of cholesterol synthesis.

These additional agents and compounds can be coordinately administered or combinatorially formulated with the analgesic agents. Accordingly, some aspects of the present invention include methods wherein the analgesic agent is administered as a pharmaceutical composition that comprises protease inhibitors, absorption enhancers, vasoconstrictors or combinations thereof. The pharmaceutical composition can be administered to the nasal cavity, oral cavity, to conjunctiva or other mucosal tissues around the eye or to the skin. The pharmaceutical composition can be administered by an intranasal route. The pharmaceutical composition can be administered by a buccal or sublingual route. The pharmaceutical composition can be administered by a transdermal route. The pharmaceutical composition can include at least one protease inhibitor, at least one absorption enhancer, at least one vasoconstrictor or combinations thereof. The pharmaceutical composition can be co-administered with a vasoconstrictor or administered after the vasoconstrictor has been delivered.

Delivery Systems

An analgesic agent or pharmaceutical composition comprising an analgesic agent may be dispensed to the buccal or sublingual surfaces in a number of different formulations or dosage forms including, but not limited to, fast-melting tablets, liquid-filled capsules, liquid sprays or lozenges. Alternatively, the pharmaceutical composition can be delivered to the mucosa of the oral cavity by direct placement of the composition in the mouth, for example, with a gel, an ointment, a dropper, or a bioadhesive strip or patch.

In some aspects of the present invention, the methods comprise administering to an individual a pharmaceutical composition wherein administration to the buccal and/or sublingual mucosal surfaces of the oral cavity is by a delivery device. The delivery device can include, but is not limited to, unit dose containers, pump sprays, droppers, squeeze bottles, airless and preservative-free sprays, nebulizers, dose inhalers and pressurized dose inhalers. The delivery device can be metered to administer an accurate effective dosage amount (as described below) to the oral cavity. In some aspects, an accurate effective dosage amount is contained within a capsule, tablet, lozenge, or bioadhesive patch that is placed directly within the oral cavity.

An analgesic agent or pharmaceutical composition may be dispensed to the conjunctiva or to other mucosal tissues around the eye in a number of different formulations such as a liquid drop, a gel, an ointment or a bioadhesive patch or strip. Thus, in some aspects of the present invention the methods comprise administering to an individual a pharmaceutical composition wherein administration is directed to the conjunctiva or other mucosal tissues around the eye. In some aspects, an accurate effective dosage amount is contained within a drop, a gel, an ointment or a bioadhesive patch that is placed directly onto the mucosal tissues around the eye.

An analgesic agent or pharmaceutical composition may be administered to the skin or scalp in a number of different formulations such as a liquid, a spray, a gel, an ointment or a bioadhesive patch or strip. Thus, in some aspects of the present invention the methods comprise administering to an individual a pharmaceutical composition wherein administration is directed to the skin of the face or scalp. In some aspects, an accurate effective dosage amount is contained within a drop, a gel, an ointment or a bioadhesive transdermal patch that is placed directly onto the skin.

An analgesic agent or pharmaceutical composition may be dispensed intranasally as a powdered or liquid nasal spray, suspension, nose drops, a gel or ointment, through a tube or catheter, by syringe, by packtail, by pledget (a small flat absorbent pad), by nasal tampon or by submucosal infusion. Nasal drug deli very can be carried out using devices including, but not limited to, unit dose containers, pump sprays, droppers, squeeze bottles, airless and preservative-free sprays, nebulizers (devices used to change liquid medication to an aerosol particulate form), metered dose inhalers, and pressurized metered dose inhalers. It is important that the delivery device protect the drug from contamination and chemical degradation. The device should also avoid leaching or absorption as well as provide an appropriate environment for storage. Each drug needs to be evaluated to determine which nasal drug delivery system is most appropriate. Nasal drug delivery systems are known in the art and several are commercially available.

The composition may be conveniently delivered in the form of an aerosol spray using a pressurized pack or a nebulizer and a suitable propellant including, but not limited to, dichlorodifluoromethane, trichlorofluoromethane, dichlorotetrafluoroethane, hydrocarbons, compressed air, nitrogen or carbon dioxide. An aerosol system requires the propellant to be inert towards the pharmaceutical composition. In the case of a pressurized aerosol, the dosage unit may be controlled by providing a valve to deliver an accurately metered amount.

The means to deliver the analgesic agent to the nasal cavity as a powder can be in a form such as microspheres delivered by a nasal insufflator device (a device to blow a gas, powder, or vapor into a cavity of the body) or pressurized aerosol canister. The insufflator produces a finely divided cloud of the dry powder or microspheres. The insufflator may be provided with means to ensure administration of a substantially metered amount of the pharmaceutical composition. The powder or microspheres should be administered in a dry, air-dispensable form. The powder or microspheres may be used directly with an insufflator which is provided with a bottle or container for the powder or microspheres. Alternatively the powder or microspheres may be filled into a capsule such as a gelatin capsule, or other single dose device adapted for nasal administration. The insufflator can have means such as a needle to break open the capsule or other device to provide holes through which jets of the powdery composition can be delivered to the nasal cavity.

Nasal delivery devices can be constructed or modified to dispense the pharmaceutical composition wherein the composition is delivered predominantly to the inferior two-thirds of the nasal cavity. For example, the angle of dispersion from a delivery device such as a nebulizer or an insufflator can be set so that the pharmaceutical composition is mechanically directed to the inferior two-thirds of the nasal cavity, and preferably away from the superior region of the nasal cavity. Alternatively, the pharmaceutical composition can be delivered to the inferior two-thirds of the nasal cavity by direct placement of the composition in the nasal cavity, for example, with a gel, an ointment, a nasal tampon, a dropper, or a bioadhesive strip.

Thus in some aspects of the present invention, the methods comprise administering to an individual a pharmaceutical composition wherein administration to the nasal cavity is by a nasal delivery device. The nasal delivery device can include, but is not limited to, unit dose containers, pump sprays, droppers, squeeze bottles, airless and preservative-free sprays, nebulizers, dose inhalers, pressurized dose inhalers, insufflators, and bi-directional devices. The nasal delivery device can be metered to administer an accurate effective dosage amount (as described below) to the nasal cavity. The nasal delivery device can be for single unit delivery or multiple unit delivery. In some aspects of the present invention, the nasal delivery device can be constructed whereby the angle of dispersion of a pharmaceutical composition is mechanically directed towards the inferior two-thirds of the nasal cavity thereby minimizing delivery to the olfactory region. The nasal delivery device can be constructed whereby the angle of dispersion of a pharmaceutical composition is mechanically directed towards the inferior two-thirds of the nasal cavity thereby maximizing delivery of the agent to opioid receptors in the trigeminal nerve. In some aspects of the present invention, the pharmaceutical composition is a gel, cream, ointment, impregnated in a nasal tampon or bioadhesive strip whereby the composition is placed in the inferior two-thirds of the nasal cavity. In some aspects of the present invention, the methods include intranasal administration of an analgesia agent wherein the administration uses a nasal delivery device with an angle of dispersion that mechanically directs the agent to the inferior two-thirds of the nasal cavity wherein the analgesic agent is administered after a vasoconstrictor. In some aspects of the present invention, the methods include intranasal administration of an analgesia agent wherein the administration uses a nasal delivery device with an angle of dispersion that mechanically directs the agent to the inferior two-thirds of the nasal cavity wherein the analgesic agent is co-administered with a vasoconstrictor.

Dosages

An analgesic agent is administered in a dose sufficient to provide a therapeutically effective amount to the trigeminal nerve system that results predominantly in analgesia to the facial or head region of an individual suffering from trigeminal nerve-associated pain. In particular, the analgesic agent can be administered in a dose that results in analgesia to the facial or head regions with minimal CNS effects or systemic side effects. The analgesic agent can be administered in a dose that results in analgesia predominantly to the facial or head regions as compared to analgesic effects in other parts of the body. A therapeutically effective dose of an analgesic agent can be determined empirically and depends on the analgesic agent, the type and severity of the pain, the route of administration, the state of disease progression, and the size/weight and overall health of the patient. In particular, a therapeutically effective dose of an analgesic agent which results in regional analgesia with minimal CNS effects or systemic side effects can be determined empirically and will depend on the same described parameters.

The amount of an analgesic agent administered as a unit dose will depend upon the type of pharmaceutical composition being administered, for example, a solution, a suspension, a gel, an emulsion, a powder, or a sustained-release formulation. Generally the effective dosage will be lower than dose amounts needed for oral, intravenous, intramuscular or subcutaneous administration of the analgesic agent involved, since targeted delivery will allow for a more concentrated level of the analgesic agent in the trigeminal nerve. The effective dosage will be lower than dosage amounts generally used for other common analgesic opioid drugs, for example, morphine. The quantity of dosage form needed to deliver the desired dose will depend on the concentration of the analgesic agent in the composition. Such determinations are within the skill of one in the art.

The therapeutic dosage of an analgesic agent in the pharmaceutical compositions used in the methods of the present invention will depend on a number of factors such as the particular analgesic agent chosen, its bioavailability by the chosen route of administration, its efficacy, and the desired frequency of administration combined with the desired single dosage of the formulation. Particularly, dosage of the analgesic agent will be chosen to maximize analgesia to the facial and head regions and minimize CNS effects or systemic side effects. Such pharmacological data can be obtained from animal models and clinical trials with normal human volunteers or patients experiencing trigeminal nerve-associated pain by one with skill in the art.

Experimental models to test for analgesic activity of agents are known in the art. Animal models comprise tests which include, but are not limited to, acetic acid writhing, phenylquinone writhing, tail-flick, paw withdrawal and ear or face withdrawal wherein the pain receptor activation is induced by such compounds as acetic acid, phenylquinone, formalin or capsaicin, or by thermal activators such as a hot plate or a laser. In particular, models for facial or head pain utilizing tests such as orofacial delivery of capsaicin, orofacial delivery of formalin, or delivery of thermal heat to the trigeminally innervated tissue, such as the face or part of the ear are available. Models can be used to determine optimal dosage ranges wherein an analgesic agent delivered to the trigeminal nerve results in analgesia in the facial or head region with minimal analgesia at a systemic site, i.e. the paw. Further, models can be used to administer an analgesic agent by a particular delivery route, e.g. intranasally, and test for analgesic effect at the ears and at the hindpaws. Thus, one model can be used to test for analgesic activity of an analgesic agent after administration of a pharmaceutical composition to the trigeminal nerve. Withdrawal latencies at the ear or face will determine localized analgesia while withdrawal latencies at the hindpaw will determine systemic distribution and analgesia.

As stated above, an effective amount of an analgesic agent will depend on the analgesic agent being used in the method. Preferably the effective amount of an analgesic agent administered transmucosally or transdermally to the trigeminal nerve is lower than dosages used when the agent is delivered by other routes (e.g. oral, intravenous, intramuscular or subcutaneous). For example, dosages used for administration of an enkephalin peptide can include, but are not limited to, an effective amount within the dosage range of about 0.01 ng per kg body weight to about 50 μg per kg body weight, or within 0.1 ng per kg body weight to about 50 μg per kg body weight, or within 1 ng per kg body weight to about 50 μg per kg body weight, or within about 10 ng per kg body weight to about 50 μg per kg body weight, or within about 0.1 μg per kg body weight to about 50 μg per kg body weight, or within about 1 μg per kg body weight to about 50 μg per kg body weight.

Dosages used for administration of an endophorin peptide can include, but are not limited to, an effective amount within the dosage range of about 0.4 μg per kg body weight to about 4 mg per kg body weight, or within 4 μg per kg body weight to about 400 μg per kg body weight, or within 4 μg per kg body weight to about 200 μg per kg body weight, or within 10 μg per kg body weight to about 100 μg per kg body weight.

Dosages used for administration of an endomorphin peptide can include, but are not limited to, an effective amount within the dosage range of about 0.15 nmol per kg body weight to about 1.5 μmol per kg body weight, or within 1.5 nmol per kg body weight to about 150 nmol per kg body weight, or within 1 nmol per kg body weight to about 100 nmol per kg body weight, or within 1 nmol per kg body weight to about 50 nmol per kg body weight.

Dosages used for intranasal administration of a dynorphin peptide can include, but are not limited to, an effective amount within the dosage range of about 10 nmol per kg body weight to about 100 μmol per kg body weight, or within 100 nmol per kg body weight to about 50 μmol per kg body weight, or within 250 nmol per kg body weight to about 25 μmol per kg body weight, or within 0.5 μmol per kg body weight to about 5 μmol per kg body weight.

Dosages used for administration of an oxytocin peptide can include, but are not limited to, an effective amount within the dosage range of about 0.1 IU to about 150 IU, or within 1 IU to about 100 IU, or within 10 IU to about 80 IU, or within about 25 IU to about 50 IU, or within about 1 IU to about 40 IU, or within about 1 IU to about 30 IU, or within about 4 IU to about 16 IU, or within about 4 IU to about 24 IU.

Dosages used for administration of octreotide can include, but are not limited to, an effective amount within the dosage range of about 0.1 mg to about 200 mg, or within 0.1 mg to about 100 mg, or within 0.5 mg to about 100 mg, or within about 0.5 mg to about 75 mg, or within about 1 mg to about 50 mg, or within about 1 mg to about 25 mg, or within about 1 mg to about 20 mg, or within about 1 mg to about 10 mg.

Dosages can be administered in a single dose or in multiple doses, for example, dosages can be administered two three, four, up to ten times daily depending on the analgesic agent and the type of pain being treated. Dosages can be administered in a sustained release formulation which allows for the analgesic agent to be administered less frequently such as six times a week, five times a week, four times a week, three times a week, twice a week, or once a week.

Thus some aspects of the present invention include methods for treating an individual for trigeminal nerve-associated pain comprising administering to the individual an effective amount of an analgesic agent wherein the administration is targeted to the trigeminal nerve system and results predominantly in analgesia to the facial or head region with minimal CNS effects or systemic side effects. The analgesic agent can be an enkephalin with a dosage range of about 0.01 ng per kg body weight to about 50 µg per kg body weight, or within 0.1 µg per kg body weight to about 50 µg per kg body weight, or within 1 ng per kg body weight to about 50 µg per kg body weight, or within about 10 ng per kg body weight to about 50 µg per kg body weight, or within about 0.1 µg per kg body weight to about 50 µg per kg body weight, or within about 1 µg per kg body weight to about 50 µg per kg body weight. The analgesic agent can be an endorphin with a dosage range of about 0.4 µg per kg body weight to about 4 mg per kg body weight, or within 4 µg per kg body weight to about 400 µg per kg body weight, or within 4 µg per kg body weight to about 200 µg per kg body weight, or within 10 µg per kg body weight to about 100 µg per kg body weight. The analgesic agent can be oxytocin with a dosage range of about 0.1 IU to about 150 IU, or within 1 IU to about 100 IU, or within 10 IU to about 80 IU, or within about 25 IU to about 50 IU, or within about 0.1 IU to about 40 IU, or within about 1 IU to about 30 M, or within about 4 IU to about 16 IU, or within about 4 IU to about 24 IU.

To determine the therapeutic effect of an analgesic agent the "visual analogue scale" (VAS) may be used to assess the reduction or alleviation of pain. VAS is a 10 cm horizontal or vertical line with word anchors at each end, such as "no pain" and "pain as bad as it could be". A subject or patient is asked to make a mark on the line to represent pain intensity. This mark is converted to distance in either centimeters or millimeters from the "no pain" anchor to give a pain score that can range from 0-10 cm or 0-100 mm. The VAS may also be set up as an 11 point numerical pain rating scale wherein 0 equals "no pain" and 10 equals the "worst pain imaginable". Using the VAS, an agent is considered to have an analgesic effect when there is a change of about 30% or more, for example a change from 9 to 7 or from 5 to 3.5.

Therapeutic Uses

Chronic, pain in the face and head region can arise from a variety of medical conditions including but not limited to neuropathic pain, headache pain, TMJ, pain from cancer and/or cancer treatment. These pain syndromes are often not effectively treated with current medications or invasive interventions and new methods for localized pain relief in the face and head regions are needed. Accordingly, some aspects of the present invention include methods for treating an individual for trigeminal nerve-associated chronic pain by administration of an analgesic agent wherein the administration is targeted to the trigeminal nerve system and results predominantly in analgesia to the facial or head region, particularly as compared to analgesic effects in other parts of the body. The analgesic agent can be administered to a patient with neuropathic pain, including but not limited to, trigeminal neuralgia, atypical facial neuralgia and post herpetic neuralgia. The analgesic agent can be administered to an individual with headache pain, for example, migraine headaches or cluster headaches. The analgesic agent can be administered to an individual with chronic pain arising from head or facial cancer or arising from previous treatment of head or facial cancer.

Local anesthesia is used for most medical, dental or cosmetic procedures wherein the procedures last a short period of time and wherein the work is isolated to the teeth, face or head. Anesthesia is generally defined as the total or partial loss of sensation, especially tactile sensibility, usually induced by use of an anesthetic compound. In addition to the pain of administration, another main disadvantage of local anesthesia is that loss of sensation results in numbness which often lasts significantly longer than the procedure. Thus there are situations wherein patients undergoing medical, dental or cosmetic procedures would benefit from short-term regional analgesia of the teeth, face or head regions. Some procedures potentially would require no other pain relieving agents or any vasoconstrictors, and the length of time of analgesia, in the absence of numbness, would be much less important than the excessive length of time of facial numbness resulting from an anesthetic. Such medical, dental and cosmetic procedures can include, but are no limited to, microdermabrasion, Botox injection, photodynamic therapy or other skin tumor ablations, hair removal (including electrolysis, laser, waxing, etc.), general facial laser treatments (including pigment removal, vascular lesions), dermal and subdermal injectable fillers (including collagen, hyaluronic acid, methylmethacrylate, hydroxyapetite, etc), facial peels by chemical or laser applications, photofacials, collagen shrinkage procedures (including radiofrequency, HIFU, high intensity light, laser, etc.), routine dental procedures, tattooing, tattoo removal, piercing and treatment of scars, keloids, etc. by steroid injection.

Thus some aspects of the present invention include methods for treating an individual for trigeminal nerve-associated pain arising from medical, dental or cosmetic procedures comprising administration of an analgesic agent wherein the administration is targeted to the trigeminal nerve system and results predominantly in analgesia of the facial or head regions. The methods can include an analgesic agent administered to an individual undergoing a procedure selected from the group comprising medical, dental and cosmetic. The methods can include medical, dental or cosmetic procedures selected from the group comprising microdermabrasion, Botox injection, photodynamic therapy or other skin tumor ablations, hair removal (including electrolysis, laser, waxing, etc.), general facial laser treatments (including pigment removal, vascular lesions), dermal and subdermal injectable fillers (including collagen, hyaluronic acid, methylmethacrylate, hydroxyapetite, etc), facial peels by chemical or laser applications, photofacials, collagen shrinkage procedures (including radiofrequency, HIFU, high intensity light, laser, etc.), dental procedures, tattooing, tattoo removal, piercing and treatment of scars and keloids by steroid injection. The analgesic agent can be administered to a patient undergoing a procedure wherein the analgesic effect lasts the length of the procedure. The analgesic agent can be administered to a patient undergoing a procedure wherein the time requirement for the procedure and for analgesia is less than 30 minutes, is less than 45 minutes, is less than 60 minutes or is less than 90 minutes. The analgesic agent can be administered to a patient undergoing a procedure wherein the time requirement for the procedure and for analgesia is more than 90 minutes.

For medical, dental or cosmetic procedures that are more extensive and will take a longer period of time, a local anesthetic is used usually in combination with a sedative to make the patient drowsy. In some cases, depending on the procedure, the patient is put under a general anesthetic. The use of local or general anesthesia does not effectively mitigate postoperative pain and analgesics are almost always delivered to the patient after the procedure is complete.

An evolving concept in operative pain management is the use of preemptive analgesia. The pain and inflammation that result from surgery normally causes increased prostaglandin production and sensitization. If analgesic agents are administered before surgery the amount of sensitization may be decreased or prevented and the degree and persistence of post-operative pain may be diminished. Therefore, there are situations wherein patients undergoing medical, dental or cosmetic procedures would benefit from regional trigeminal or facial analgesia prior to the procedure, during the procedure and during the post-operative period. Some procedures typically benefit by the use of vasoconstrictors, for example, before plastic surgery to decrease the amount of bleeding at an incision site. Therefore one level of benefit from facial analgesia would be the elimination of pain associated with an injection of a vasoconstrictor, wherein the time required for analgesia could be, less than 10 minutes. Another level of benefit exists if the facial analgesia starts before the surgery starts, lasts throughout the entire procedure and continues into the post-operative period, wherein the post-operative period could represent hours or days. Examples of dental procedures may include, but are not limited to, major dental procedures such as periodontal, reconstructive, palatal, tooth extraction, root canal surgery, etc. Examples of cosmetic or medical surgical procedures may include, but are not limited to, facelift, blepharoplasty, browlift, rhinoplasty, cheek implant, chin implant, fat injections, lesion removal, excisional biopsies, Mohs surgery (micrographic surgery for skin cancer), flap reconstruction, orthognathic (correction of jaw deformities), ophthalmic and oculoplastic (plastic surgery of the eye), hair replacement surgery, extensive laser resurfacing, trauma such as laceration repair, nasal fracture repair, facial bone fracture repair, burn debridement and wound cleaning.

Accordingly, some aspects of the present invention include methods for treating an individual for trigeminal nerve-associated pain arising from medical, dental or cosmetic procedures comprising administration of an analgesic agent wherein the administration is targeted to the trigeminal nerve system and results in localized analgesia of the face, head or teeth. The methods can include an effective dosage amount wherein the localized analgesia lasts for the length of the procedure and continues into a post-operative period. The methods can include medical, dental or cosmetic procedures selected from the group comprising periodontal surgery, reconstructive tooth surgery, palatal surgery, tooth extraction, root canal surgery, facelifts, blepharoplasties, browlifts, rhinoplasties, cheek implants, chin implants, fat injections, lesion removal, excisional biopsies, Mohs surgery, flap reconstruction, orthognathic surgery, ophthalmic surgery, oculoplastic surgery, hair replacement surgery, extensive laser resurfacing, laceration repair, nasal fracture repair, facial bone fracture repair, burn debridement and wound cleaning. The analgesic agent can be administered to a patient undergoing a medical procedure prior to injection of a vasoconstrictor into the facial or head region. The analgesic agent can be administered to a patient undergoing a medical procedure wherein the analgesia lasts beyond the length of the procedure and into a post-operative time period. The analgesic agent can be administered to a patient undergoing a medical procedure wherein the analgesia lasts for hours to days after the medical procedure is finished.

Kits

Provided herein are kits for use in carrying out any of the methods described herein. Kits are provided for use in treatment of trigeminal nerve-associated pain. Kits of the invention may comprise at least one analgesic agent in suitable packaging. Kits may further comprise a vasoconstrictor, at least one protease inhibitor and/or at least one absorption enhancer. Kits may further comprise a delivery device, including but not limited to, a device for intranasal administration. Kits may further comprise instructions providing information to the user and/or health care provider for carrying out a method described herein.

Kits comprising a single component will generally have the component enclosed in a container (e.g., a vial, ampoule, or other suitable storage container). Likewise, kits including more than one component may also have the additional reagents in containers (separately or in a mixture).

The instructions relating to the use of the kit generally describe how the contents of the kit are used to carry out the methods of the invention. Instructions supplied in the kits of the invention are typically written instructions on a label or package insert (e.g., a paper sheet included in the kit), but machine-readable instructions (e.g., instructions carried on a magnetic or optical storage disk) are also acceptable.

EXAMPLES

Example 1

One way to test activity of an analgesic agent in a rat model is by treatment-induced changes in latencies (times) of withdrawal in response to noxious heating of the skin, typically using an ear, the face or a hindpaw. Thus, application of coherent or non-coherent (non-laser) radiant heat to the ear, the face or hindpaw will elicit rapid withdrawal movements. Latencies of withdrawal have been demonstrated to be sensitive to analgesic treatments, such that analgesics increase the latency to withdrawal. Transmucosal or transdermal administration of analgesic agents to the trigeminal nerve to reduce trigeminal nerve-associated pain can be tested for regional and/or systemic analgesia. The rostral external part of a rat's ear is innervated by a branch of the mandibular nerve, itself a branch of the trigeminal nerve, thus after treatment an increase in latency to withdrawal time would indicate regional analgesia. A change in the latency to withdrawal time of the hindpaw would indicate whether there was a systemic analgesic effect, i.e. no change in the latency to withdrawal time indicates no systemic effect, while an increase in latency to withdrawal time would indicate a systemic effect.

Rats are housed in a 12/12-hour light/dark environment and are provided food and water ad libitum. Efforts are made to minimize discomfort and reduce the number of animals used. Rats are lightly anesthetized with urethane and placed with minimal restraint on a heating pad to maintain their body temperature at 37° C. A laser beam is directed via a fiberoptic cable to the rostral external part of both ears. Characteristic responses to laser irradiation are a retraction or withdrawal of the stimulated ear for 1-3 seconds after a thermal stimulus by the laser. Laser stimulation is terminated rapidly after response of the stimulated ear or after a maximal response (cut-off) latency of 30 seconds to prevent tissue damage.

For baseline testing of latency withdrawal responses to the ear, 3 pulses are applied to the portion of each ear that is innervated by the trigeminal nerve. The stimulation site is changed after each pulse allowing at least 2 minutes in between 2 stimuli on the same ear. For baseline testing of latency withdrawal responses to the hindpaw, 3 pulses are applied to the hindpaw. The stimulation site is changed after each pulse allowing at least 2 minutes in between 2 stimuli on the same hindpaw. Testing sessions are videotaped for off-line analysis of responses. The off-line analysis is performed by an investigator who determines the latency of withdrawal responses to the laser stimulation and who is blinded to the treatment groups.

After measuring baseline latencies, analgesic agents are administered intranasally. This involves 5 equal 10 µl applications to the nose by pipette for a total volume of 50 µl over 20 minutes. The effect of different doses of an agent (e.g. 10 nmoles/kg met-enkephalin) on latency responses is examined. To assess the local analgesic effect, the latency responses of the ear are tested at various time points after agent administration. To assess the systemic analgesic effect, the latency responses of hindpaws are tested at various timepoints after agent administration.

Example 2

Figure 1B:
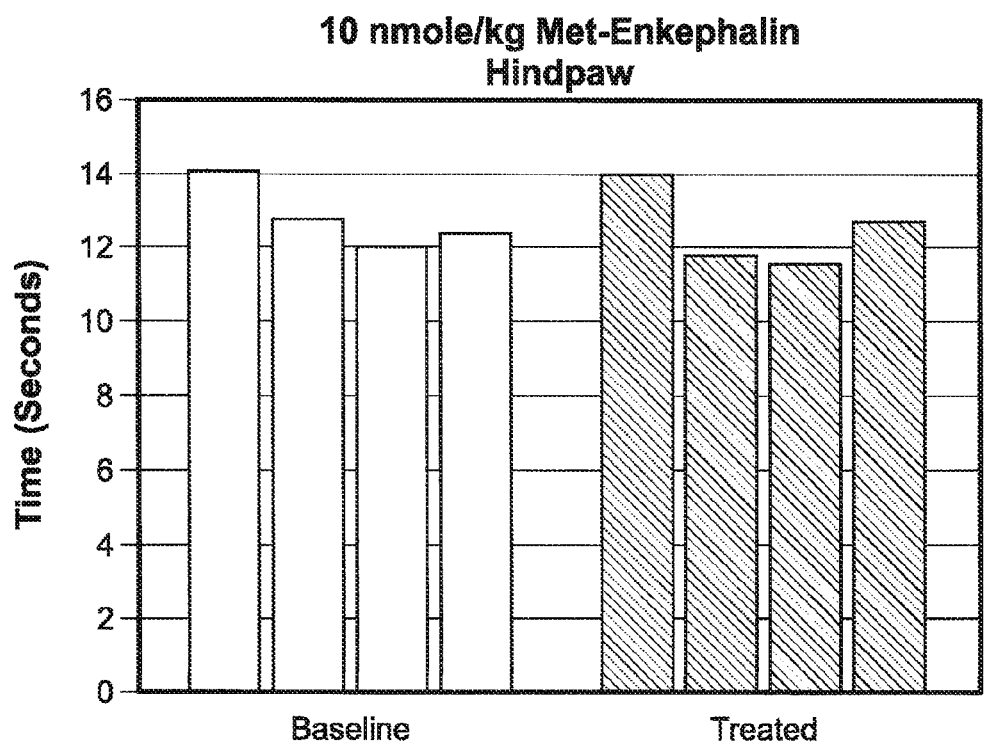

Sprague-Dawley rats (Charles River Laboratories) were lightly anesthetized with urethane and placed with minimal restraint on a heating pad to maintain their body temperature at 37° C. A laser beam was directed via a fiberoptic cable to the rostral external part of both ears or to the hindpaws as described above. Baseline withdrawal latencies were measured by delivering 4 separate stimuli with a resting period of approximately 15 minutes between each stimulus. 50 µl of met-enkephalin in phosphate-buffered saline was intranasally administered in 5 equal 10 µl applications at a dosage of 10 nmoles/kg of body weight. Withdrawal latencies for both ears and hindpaws were tested five minutes after the final application of met-enkephalin. As described above, testing sessions were videotaped and analyzed. Results demonstrated that intranasal administration of met-enkephalin at this dosage achieved a regional analgesic effect in the head region (FIG. 1A) without a systemic analgesic effect at the hindpaw (FIG. 1B).

Example 3

Normal Human Volunteers

Regional analgesia in the face region after administration of analgesic agents by intranasal delivery can be tested in normal subjects. Study participants are selected based on inclusion/exclusion criteria, history and physical exam, laboratory tests, and other customary procedures. Thermal pain responses are elicited on the face, in particular the cheek, and on the hand of healthy normal volunteers, such that temperature thresholds for evoking pain and/or the temperature of maximal pain tolerance can be assessed and baselines established. Increasing doses of an analgesic agent are administered to the subjects and a dose-response curve is calculated for each stimulation site. Changes in thermal pain threshold and tolerance at the two sites can be compared so that the efficacy of an analgesic agent at a given dose in affecting facial and whole-body pain can be determined.

The analgesic agent is delivered intranasally to the subjects by a metered dose nebulizer. For example, a dose of 0.01 µg/kg of oxytocin in 0.1 ml of saline is administered with each nasal puff application to the subjects. 0.1 ml of saline only with each nasal puff application is administered to control subjects. It is determined what doses of an analgesic agent administered to the trigeminal nerve are effective for establishing regional analgesia in the facial region (i.e. the cheek) with minimal systemic distribution and minimal or no analgesic effect at the peripheral site (i.e. the hand).

Example 4

Human Patients

Patients undergoing cosmetic facial surgery normally experience significant post-operative pain. The patients are treated with an analgesic agent which is administered intranasally by metered dose nebulizer at the cessation of surgery. Patients receive a dose of a test agent (e.g. 0.01 µg/kg of oxytocin) in 0.1 ml of normal saline or they receive a placebo of saline alone. A patient's facial pain ratings are then determined on the visual analogue scale (VAS) at 10 minute intervals for 2 hours. A second set of patients undergoing a similar surgical procedure to the hand also receive an intranasal application of either the test agent or saline placebo. Patient's hand pain ratings are then determined on the visual analogue scale (VAS) at 10 minute intervals for 2 hours.

Example 5

Sprague-Dawley rats (Charles River Laboratories) were anesthetized with isofluorane and a platinum electrode was inserted transcranially into the trigeminal ganglion. Nerve impulses (action potential) were recorded from single pain sensing nerve cells in the trigeminal ganglion in response to application of noxious laser pulses to the face of the rats. After recording responses to several identical laser pulses, 10 nmoles of oxytocin was applied to the nose of the rats. Thereafter, identical laser pulses were once again applied and recorded.

Figure 2:
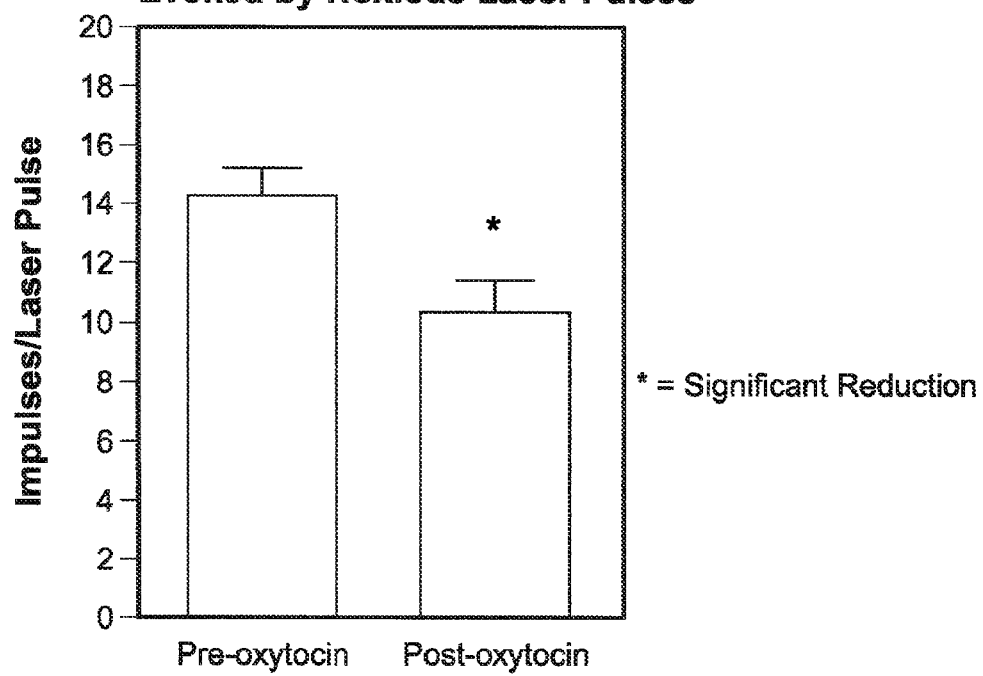
FIG. 2 depicts the effect of intranasal administration of oxytocin on trigeminal nerve impulses in response to noxious laser pulses to the face in a rat model. Data demonstrating average nerve impulses after noxious laser pulses to the face pre- and post-treatment are shown.

FIG. 2 shows the average nerve impulses per a laser pulse for pre-oxytocin and post-oxytocin treatment. Oxytocin significantly ($p<0.05$) reduced the neuronal response to noxious laser pulses applied to the animal's face. These data showed that at least part of the analgesic effect of nasal application of oxytocin was by way of direct inhibition of neurons in the trigeminal nerve.

Example 6

Male Sprague-Dawley rats (Charles River Laboratories) were anesthetized with isoflurane and used in the following experiments. In the anesthetized rats, single unit, extracellular recordings were performed in trigeminal nucleus caudalis while stimulating the ipsilateral facial skin with constant-current bipolar electrical stimulation. Epoxylate-insulated, tungsten microelectrodes (10 MOhm) were used under stereotaxic coordinate control.

FIG. 3 demonstrates the effect of intranasal oxytocin electrical stimulation-induced responses of trigeminal nucleus caudalis wide dynamic range (WDR) neurons. Shown are responses (action potentials per 30 stimuli) to repeated stimulation of a rat's face before oxytocin administration (pre-oxytocin). After administration with oxytocin at approximately 0.1 IU, responses were recorded every five minutes for 65 minutes. A second administration of oxytocin at the same dosage was administered at approximately 70 minutes after the first dose. The approximate site of the administration of the electrical stimulation is indicated by the black spot on a map of the rat's face (FIG. 3B). FIG. 3C shows raw data recorded during electrical stimulation before oxytocin administration. FIG. 3D shows raw data recorded during electrical stimulation 30 minutes after intranasal oxytocin administration.

Figure 3A:
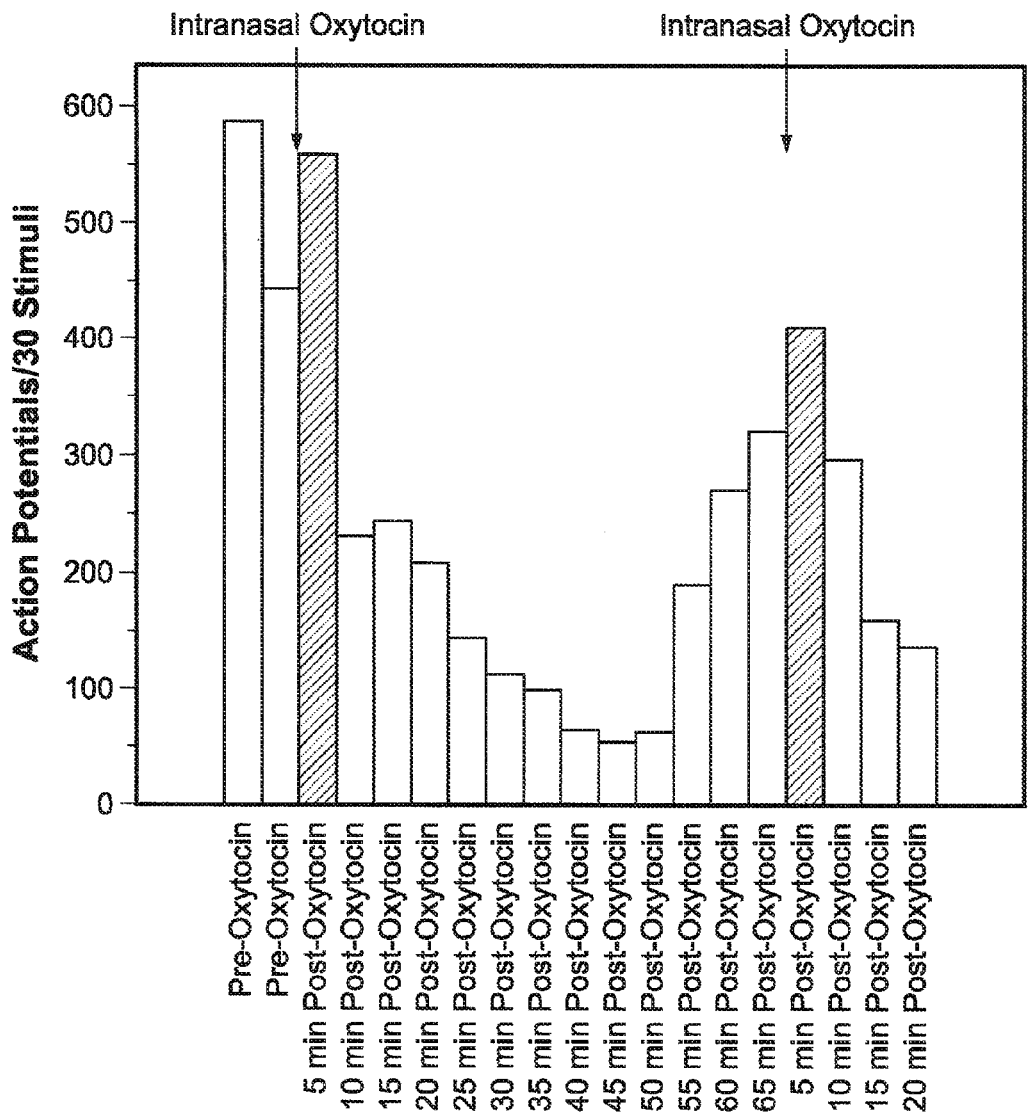
FIG. 3A shows responses (action potentials per 30 stimuli) to repeated stimulation of a rat's face before and after oxytocin administration.
Figure 3B:
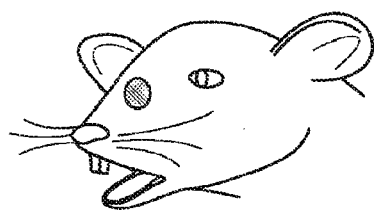
FIG. 3B shows the approximate site (black spot) of administration on the rat's face of the electrical administration.
Figure 3C:
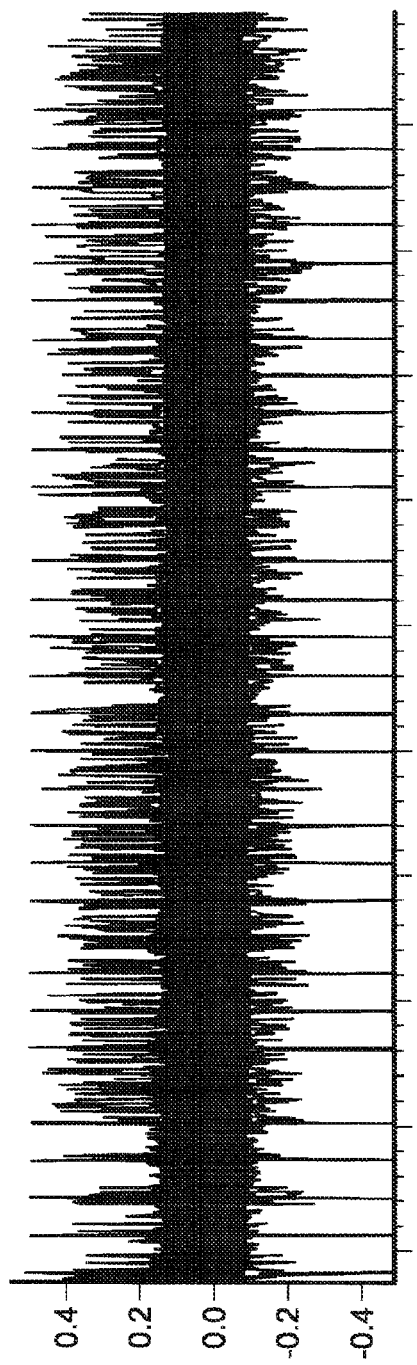
FIG. 3C shows raw data recorded during electrical stimulation before oxytocin administration.
Figure 3D:
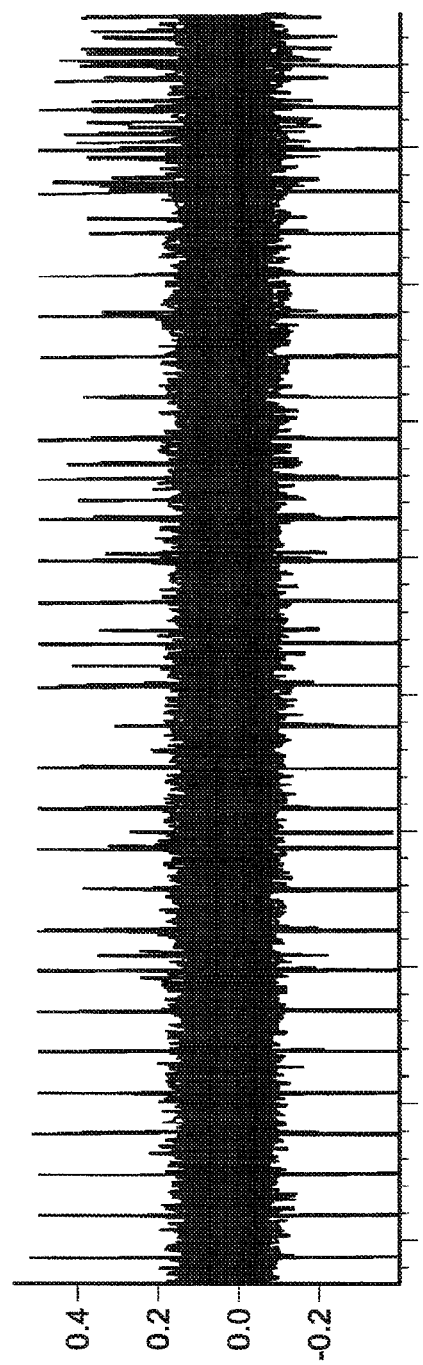
FIG. 3D. shows raw data recorded during electrical stimulation 30 minutes after intranasal oxytocin administration.
Figure 4A:
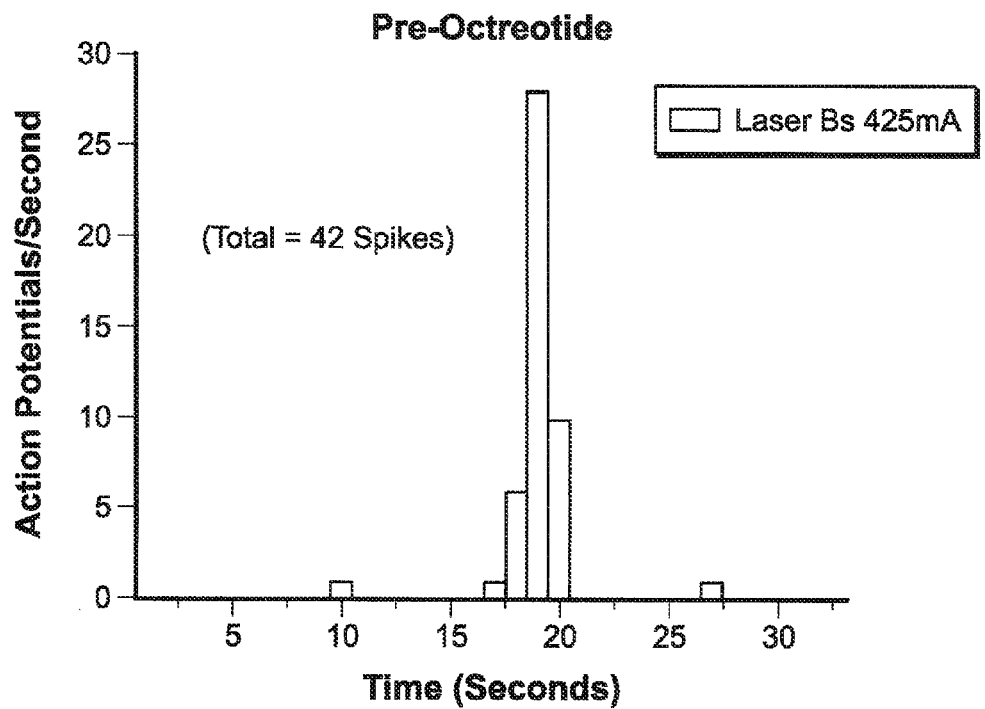
FIG. 4A shows a baseline response before administration with octreotide.
Figure 4B:
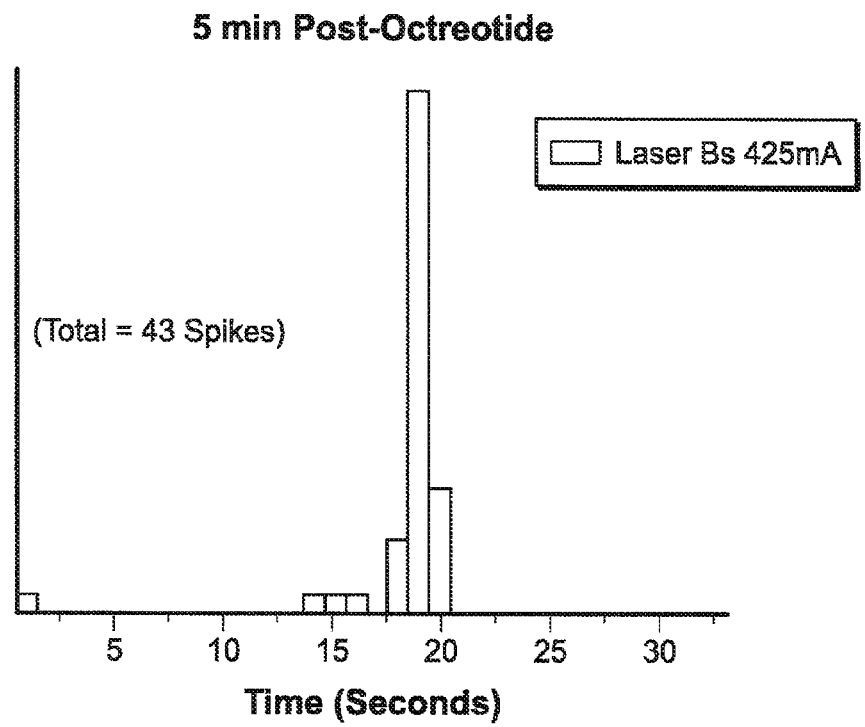
FIG. 4B shows responses 5 minutes after octreotide administration.
Figure 4C:
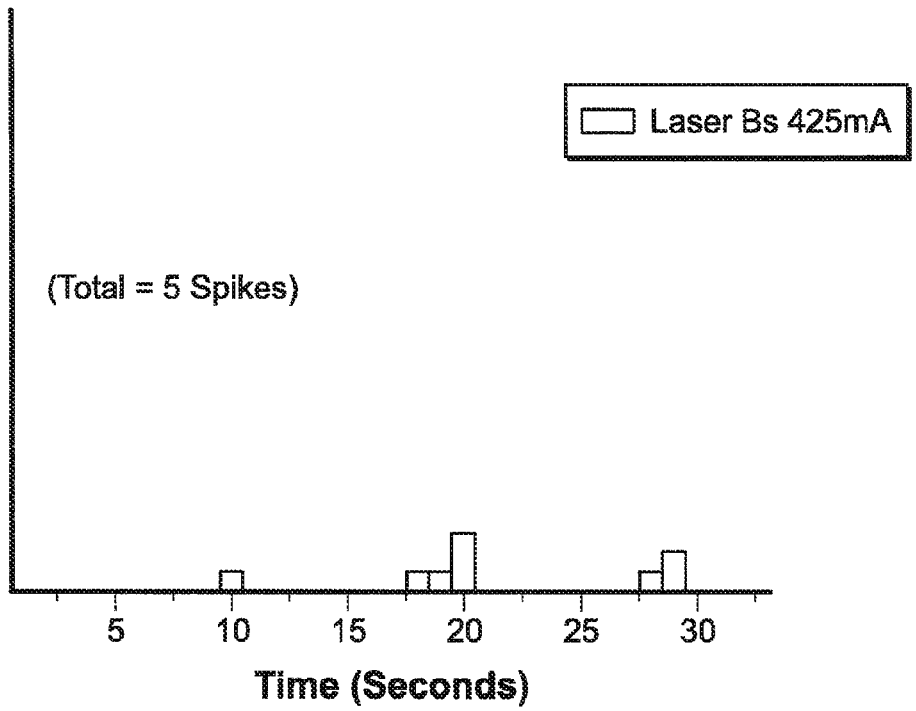
FIG. 4C shows responses 10 minutes after octreotide administration.
Figure 4D:
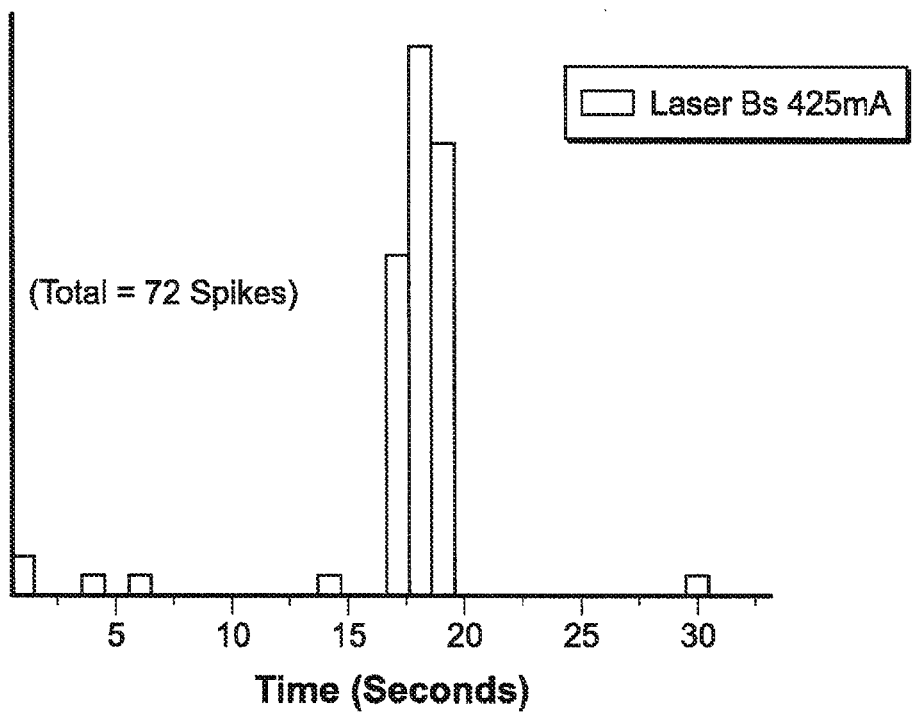
FIG. 4D shows responses 25 minutes after octreotide administration.
Figure 4E:
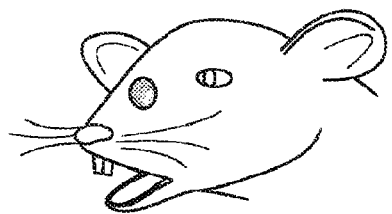
FIG. 4E shows the approximate site (black spot) of administration on the rat's face of the electrical administration

Oxytocin treatment caused a significant reduction in responses beginning 10 minutes after a first administration and continued until 50 minutes post treatment when responses began to increase (FIG. 3A). At approximately 70 minutes after the first treatment, a second dose of oxytocin was administered. Within 10 minutes, the second oxytocin treatment caused a significant reduction in responses. These data demonstrated that intranasal administration of oxytocin could cause a large effect (i.e. reduction in action potentials) but also that the effect was reproducible within a short period of time.

Example 7

Male Sprague-Dawley rats (Charles River Laboratories) were anesthetized with isoflurane and used in the following experiments. In the anesthetized rats, single unit, extracellular recordings were performed in trigeminal nucleus caudalis while stimulating the ipsilateral facial skin with diode laser or constant-current bipolar electrical stimulation. Epoxylate-insulated, tungsten microelectrodes (10 MOhm) were used under stereotaxic coordinate control.

FIG. 4 demonstrates the effect of intranasal octreotide on long-pulse laser-induced responses of trigeminal nucleus caudalis wide dynamic range (WDR) neurons. Shown are responses (action potentials per second) to an 8 second-duration, 425 mA intensity laser stimulus to the site indicated by the black spot on a map of the rat's face (FIG. 4E). FIG. 4A shows a baseline response before treatment (pre-octreotide). FIG. 4B shows response 5 minutes after octreotide treatment (0.025 ml of 0.05 mg/ml). FIG. 4C shows the response ten minutes after octreotide treatment. FIG. 4D shows the respond 25 minutes after octreotide treatment.

There was no detectable reduction in response five minutes post-octreotide treatment, but the response at 10 minutes post-treatment was reduced from 42 to 5 spikes, a reduction of 88%. The response had recovered by 25 minutes post-treatment. These data show that intranasally administered octreotide can reduce the responses of pain-transmitting neurons in the trigeminal sensory system.

Example 8

Figure 5A:
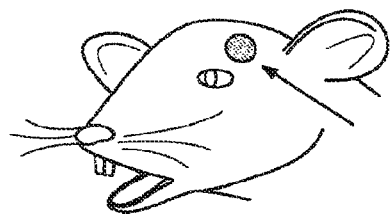
FIG. 5A shows the approximate site (black spot) of administration on the rat's face of the electrical administration.
Figure 5B:
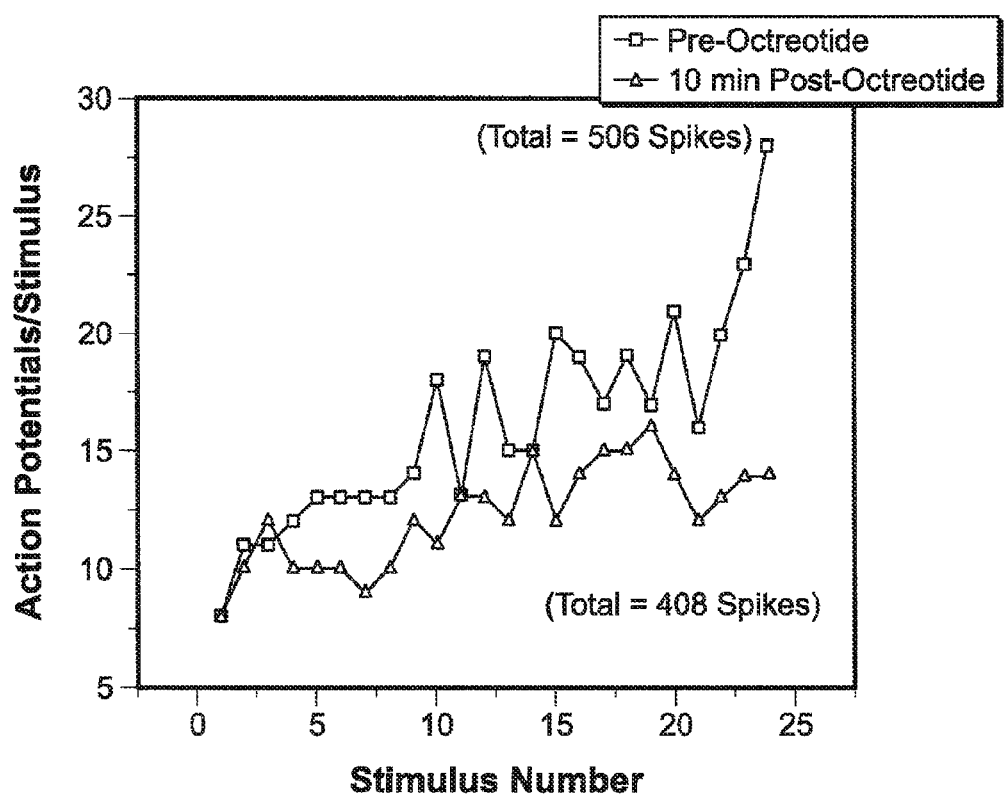
FIG. 5B shows responses before (solid squares) and 10 minutes after (open triangles) an intranasal administration of octreotide.

Male Sprague-Dawley rats (Charles River Laboratories) were anesthetized with isoflurane and used in the following experiments. FIG. 5 demonstrates the effect of intranasal octreotide on electrical stimulus-induced windup. Windup is the phenomenon by which multiple, consecutive, supramaximal stimuli of constant-intensity electrical stimuli evoke progressively greater responses by the neuron, and has been shown to be a good model for testing central neuronal excitability. Needle electrodes were inserted subcutaneously at the site indicated in FIG. 5A by the black spot on the rat's head, and the skin was stimulated at 0.66 Hz, 2 msec duration, 3×C-fiber threshold for >25 times. FIG. 5B shows the responses (spikes/stimulus) to 25 stimulations before (solid squares) and 10 minutes after (open triangles) an intranasal administration of octreotide (0.025 ml of 0.05 mg/ml).

The total number of action potentials during the stimulation period was reduced from 506 before octreotide treatment to 408 10 minutes after octreotide administration, a reduction of 19.4%. FIGS. 5C-5F depict raw data sweeps during the same recording period and electrical stimulation. FIGS. 5C and 5D depict the responses to the $1^{st}$ and $15^{th}$ stimuli before octreotide administration, and FIGS. 5E and 5F depict the responses to the $1^{st}$ and $15^{th}$ stimuli 10 minutes post-octreotide administration. This data demonstrates that octreotide can modulate neuronal excitability of second-order neurons in the trigeminal nucleus caudalis.

Although the foregoing invention has been described in some detail by way of illustration and example for purposes of clarity of understanding, it will be apparent to those skilled in the art that certain changes and modifications may be practiced without departing from the invention. Therefore, the descriptions and examples should not be construed as limiting the scope of the invention.

All publications, patents, and patent applications cited herein are hereby incorporated by reference in their entirety.

We claim:

1. A method of treating chronic head or facial pain associated with the trigeminal nerve in an individual in need thereof comprising intranasally administering an effective dose of an oxytocin peptide, wherein the head or facial pain arises from atypical facial pain, cancer, infection, a burn, a laceration, a broken bone, a toothache, temporomandibular joint disorder (TMJ), a dental procedure, a medical surgical procedure or a cosmetic procedure.

2. The method of claim 1, wherein the chronic head or facial pain arises from a dental procedure, a medical surgical procedure or a cosmetic procedure.

3. The method of claim 1, wherein the chronic head or facial pain arises from TMJ.

4. The method of claim 1, wherein the chronic head or facial pain arises from a dental procedure.

5. The method of claim 1, wherein the oxytocin peptide is administered to the inferior two-thirds of the nasal cavity.

6. The method of claim 1, wherein the oxytocin peptide is administered as a pharmaceutical formulation.

7. The method of claim 6, wherein the pharmaceutical formulation further comprises at least one protease inhibitor or at least one absorption enhancer.

8. The method of claim 1, further comprising administering a second analgesic agent.

9. The method of claim 8, wherein the second analgesic agent is administered intranasally.

10. The method of claim 1, further comprising administering a vasoconstrictor.

11. The method of claim 10, wherein the vasoconstrictor is administered intranasally.

12. The method of claim 8, wherein the second analgesic agent is nociceptin/orphanin FQ.

13. The method of claim 6, wherein the pharmaceutical formulation further comprises at least one protease inhibitor and at least one absorption enhancer.

14. The method of claim 6, wherein the pharmaceutical formulation further comprises one or more pharmaceutically acceptable excipients, adjuvants, diluents or stabilizers.

15. The method of claim 6, wherein the pharmaceutical formulation is administered as a powder, a gel, a film, an ointment, a liquid, a suspension, a cream or a bioadhesive.

16. The method of claim 1, wherein the effective dose is about 0.1 IU to about 150 IU.

17. The method of claim 1, wherein the effective dose is about 1 IU to about 100 IU.

18. The method of claim 1, wherein the effective dose is about 10 IU to about 80 IU.

19. The method of claim 1, wherein the effective dose is about 4 IU to about 24 IU.

* * * * *